(12) United States Patent
Yu et al.

(10) Patent No.: US 7,083,648 B2
(45) Date of Patent: Aug. 1, 2006

(54) TISSUE LOCKABLE CONNECTING STRUCTURES

(75) Inventors: Chang Yu, Winterville, NC (US); Glenn Harris, Greenville, NC (US)

(73) Assignee: East Carolina University, Greenville, NC (US)

( * ) Notice: Subject to any disclaimer, the term of this patent is extended or adjusted under 35 U.S.C. 154(b) by 0 days.

(21) Appl. No.: 10/398,887

(22) PCT Filed: Nov. 30, 2000

(86) PCT No.: PCT/US00/32606

§ 371 (c)(1),
(2), (4) Date: Jul. 9, 2003

(87) PCT Pub. No.: WO02/38083

PCT Pub. Date: May 16, 2002

(65) Prior Publication Data

US 2003/0236575 A1     Dec. 25, 2003

Related U.S. Application Data

(60) Provisional application No. 60/244,735, filed on Oct. 31, 2000.

(51) Int. Cl.
*A61F 2/10*     (2006.01)

(52) U.S. Cl. ..................... 623/15.11; 604/174

(58) Field of Classification Search .................. 604/93, 604/73, 174–175; 623/15.11–15.12
See application file for complete search history.

(56) References Cited

U.S. PATENT DOCUMENTS

| | | | |
|---|---|---|---|
| 3,783,868 A * | 1/1974 | Bokros | 604/891.1 |
| 4,265,244 A * | 5/1981 | Hill | 604/175 |
| 4,416,028 A * | 11/1983 | Eriksson et al. | 623/1.38 |
| 4,496,349 A | 1/1985 | Cosentino | |
| 4,634,422 A | 1/1987 | Kantrowitz et al. | |
| 4,863,474 A * | 9/1989 | Brown et al. | 623/23.54 |
| 4,897,081 A * | 1/1990 | Poirier et al. | 604/175 |
| 4,946,444 A * | 8/1990 | Heimke et al. | 604/175 |
| 5,098,397 A | 3/1992 | Svensson et al. | |
| 5,219,361 A | 6/1993 | von Recum et al. | |
| 5,348,788 A | 9/1994 | White | |
| 5,569,462 A | 10/1996 | Martinson et al. | |
| 5,593,440 A | 1/1997 | Brauker et al. | |
| 5,626,561 A | 5/1997 | Butler et al. | |
| 5,888,232 A | 3/1999 | Taylor | |
| 5,931,872 A | 8/1999 | Lohmann | |
| 6,008,430 A | 12/1999 | White | |
| 6,008,431 A | 12/1999 | Caldarise et al. | |
| 6,010,336 A | 1/2000 | Shimotoso et al. | |
| 6,077,076 A | 6/2000 | Comfort | |
| 6,213,973 B1 * | 4/2001 | Eliasen et al. | 604/93.01 |
| 6,726,660 B1 * | 4/2004 | Hessel et al. | 604/175 |
| 2004/0230092 A1 * | 11/2004 | Thierfelder et al. | 600/37 |

FOREIGN PATENT DOCUMENTS

WO    WO 97/06755    2/1997
WO    WO98/43559    10/1998

OTHER PUBLICATIONS

Amano, Isumi et al., Development of Alumina Ceramic Transcutaneous Connector to Prevent Skin Exit site Infections Around CAPD Catheters, Trans. Amer. Soc. Artif. Int. Organs, 1990, pp. M494-M496, vol. 36.

Arabia, F.A., et al., Success Rates of Long-Term Circulatory Assist Devices Used Currently for Bridge to Hear Transplantation, Trans. Amer. Soc. Artif. Int. Organs, 1996, pp. M542-M546, vol. 42.

Bailie, M.B. et al., Vascular-Access-Port Implantation for Serial Blood Sampling in Conscious Swine, Laboratory Animal Science, Aug. 1986, pp 431-433, vol. 36, No. 4.

Daly, Benedict D.T. et al., A New Percutaneous Access Device for Peritoneal Dialysis, Trans. Amer. Soc. Artif. Int. Organs, 1987, pp. 664-671, vol. XXXIII.

Daly, Benedict D.T., Percutaneous Access for Perifoneal Dialysis, Trans. Amer. Soc. Artif. Int. Organs, 1988, pp. 932-934.

Fernie, G. R. et al., A Percutaneous Implant Using a Porous Metal Surface Coating for Adhesion to Bone and a Velour Covering for Soft Tissue Attachment: Results of Trials in Pigs, J. Biomed. Mater. Res., 1977, pp. 883-891, vol. 11.

Hall, C. William et al., A Permanently Attached Artificial Limb, Trans. Amer. Soc. Artif. Int. Organs, 1967, pp. 329-331, vol. XIII.

Herrmann, Virginia M., Permanently Implanted Devices for Drug Infusion, Trans. Amer. Soc. Artif. Int. Organs, 1988, pp. 934-936, vol. 34.

Irsigler, K et al., Long-term Continuous Intraperitoneal Insulin Infusion with an Implanted Remote-Controlled Insulin Infusion Device, Diabetes, Dec. 1981, pp. 1072 1075, vol. 30.

Kantrowitz, A. et al., Development of a Percutaneous Access Device, Trans. Amer. Soc. Artif. Int. Organs, 1980, pp. 444-449, vol. XXVI.

Kantrowitz, Adrian et al., A Mechanical Auxiliary Ventricle, Histologic Responses to Long-Term, Intermittent Pumping in Calves, Trans. Amer. Soc. Artif. Int. Organs, 1995, pp. M340-M345, vol. 41.

Kantrowitz, Adrian et al., Development of a New Long-term Access Device for Continuous Ambulatory Peritoneal Dialysis, Trans. Amer. Soc. Artif. Int. Organs, 1988, pp. 930-931, vol. XXXIV.

Levy, William, Amputees: Skin Problems and Prostheses, Continuing Medical Education, May 1995, pp. 297-301, vol. 55.

Lundgren, Dan et al., Soft-Tissue-Anchored Percutaneous Device for Long-Term Intracorporeal Access, Journal of Investigative Surgery, 1989, pp. 17-27, vol. 2.

Murphy, Eugene F., History and Philosophy of Attachment of Prostheses to the Musculo-Skeletal System and of Passage through the Skin with Inert Materials, J. Biomed. Mater. Res. Symposium, 1973, pp. 275-295, No. 4.

Mussivand, Toly et al., A Transcutaneous Energy and Information Transfer System for Implanted Medical Devices, Trans. Amer. Soc. Artif. Int. Organs, 1995, pp. M253-M258, vol. 41.

Paquay, Yvonne C. et al., A One Stage Versus Two Stage Surgical Technique, Tissue Reaction to a Percutaneous Device Provided With Titanium Fiber Mesh Applicable for Peritoneal Dialysis, Trans. Amer. Soc. Artif. Int. Organs, 1996, pp. 961-967, vol. 42.

Phillips, Richard P., A High Capacity Transcutaneous Energy Transmission System, Trans. Amer. Soc. Artif. Int. Organs, 1995, pp. M259-M262, vol. 41.

Sanders, Gloria T., Lower Limb Amputations: A Guide to Rehabilitation, 1986, pp. 546-556, Philadelphia: Davis.

Shin, Yoshiharu et al., Tissue Reactions to Various Percutaneous Materials with Different Surface Properties and Structures, International Society for Artificial Organs, 1997, pp. 995-1001, vol. 21, No. 9.

Swartz, Marc T. et al., Evaluation of an implantable Ventricular Assist System for Humans With Chronic Refractory Heart Failure, Trans. Amer. Soc. Artif. Int. Organs, 1995, pp. 27-31, vol. 41.

Topaz, Peter A. et al., Molded Double Lumen Silicone Skin Button for Drivelines to an Artificial Heart, 1991, pp. M222-M223.

Voos, Kurt et al., Use of a Tobramycin-Impregnated Polymethylmethacrylate Pin Sleeve for the Prevention of Pin-Tract Infection in Goats, Journal of Orthopaedic Trauma, 1999, pp. 98-101, vol. 13, No. 2.

Wredling, R. et al., Experience of Long-Term Intraperitoneal Insulin Treatment Using a New Percutaneous Access Device, Diabetic Medicine, 1991, vol. 8, pp. 597-600.

Yu, Chang et al., The LPD-11: A Modified Locked Percutaneous Device that Permits Safe Subcutaneous Access, Trans. Amer. Soc. Artif. Int. Organs, 2001, pp. 25-29, vol. 47.

PCT International Search Report, International Application No. PCT/US00/32606 dated Mar. 21, 2001.

Yu, Chang et al., *A novel percutaneous barrier device that permits safe subcutaneous access*, ASAIO Journal 45(6); 531-534, 1999.

Yu, Chang et al., *An alternative design of locked percutaneous device (LPD), for skeletal extension through skin*. Artificial Organs 27(3): 267-271, 2003.

* cited by examiner

*Primary Examiner*—Suzette J-J Gherbi
(74) *Attorney, Agent, or Firm*—Myers Bigel Sibley & Sajovec PA

(57) ABSTRACT

Percutaneous skin access devices include a plurality of locked connecting units mounted to the exterior surface of an implantable medical object which, in position, is configured to penetrate the skin of a subject. The locked connecting units may be mounted directly onto the desired surface of the exterior of the device or may be held on a substrate sheet, which is mounted to the exterior surface of the device. In position, the locked connecting units engage with soft tissue which can include the skin to form a bio-junction layer which includes mechanical and bio-sealing connection between the device body and the soft tissue. The configuration at the bio-junction layer secures the medical object in location in the subject even for long-term indwelling applications in a manner, which inhibits soft tissue infection.

The locked connecting units may be rigid or semi-rigid for longer-term indwelling applications, and semi-rigid and/or resilient for shorter term indwelling applications. The locked connecting units may take on the form of rings, hooks, or loops having aperture or gap width/length sizes of from about 0.2–4 mm. The rings, loops, or hooks may connect with any soft tissue including skin as well subcutaneous tissue. The rings, hooks, or loops may be released from the skin/tissue without requiring surgical cutting procedures.

The locked connecting units may be configured as a semi-rigid mesh collar arranged about the primary body providing access to the subject such that it resides in the subject and engages with the skin (epidermal/dermal layer). The mesh collar can be described as a particular type of ring or loop structure as the mesh defines the gap provided in individual loop configurations. The mesh collar may be used alone, or in combination with the loops, rings, or hooks. A skin stop collar having increased rigidity may be disposed under the mesh collar.

32 Claims, 14 Drawing Sheets

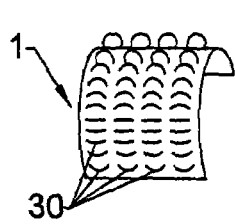 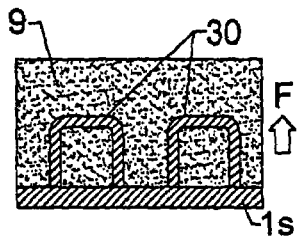 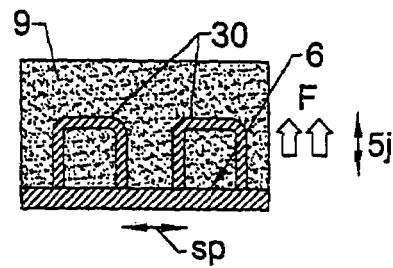
FIG. 3A.  FIG. 3B.  FIG. 3C.
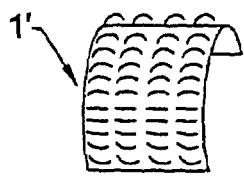 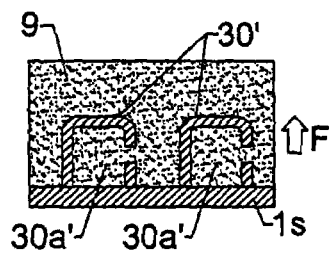 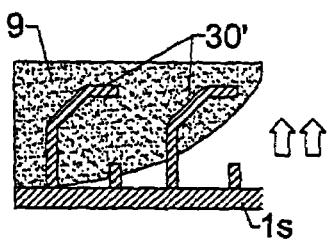
FIG. 4A.  FIG. 4B.  FIG. 4C.
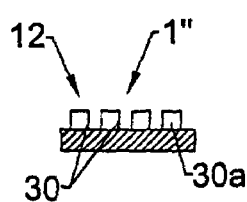 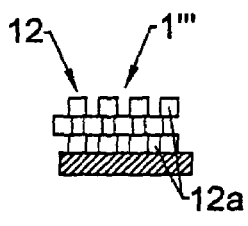 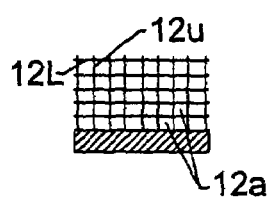
FIG. 5A.  FIG. 5B.  FIG. 5C.
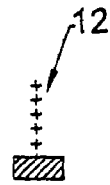  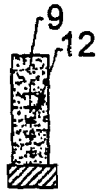
FIG. 5D.  FIG. 5E.  FIG. 5F.
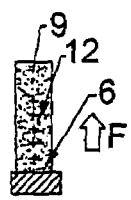
FIG. 5G.

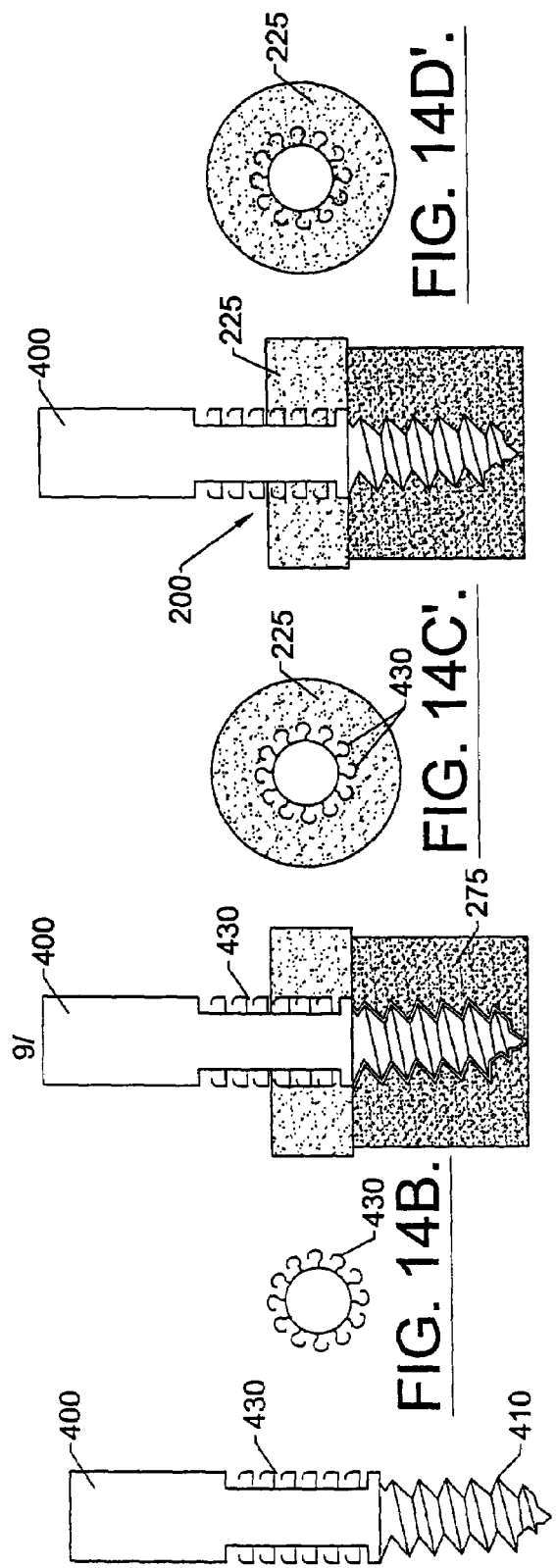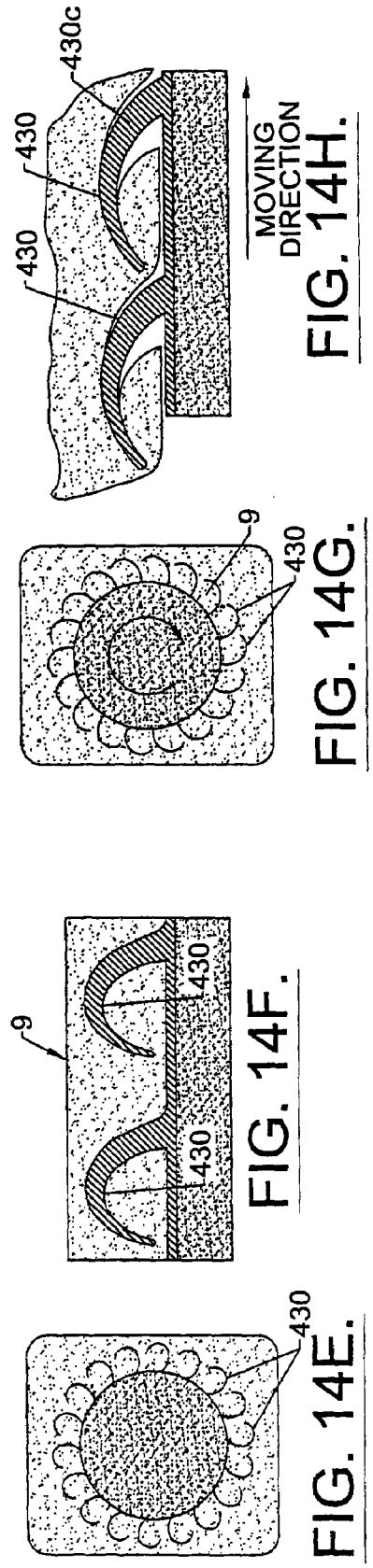

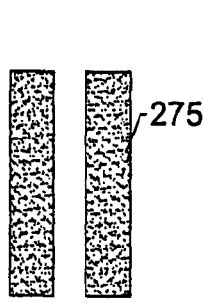 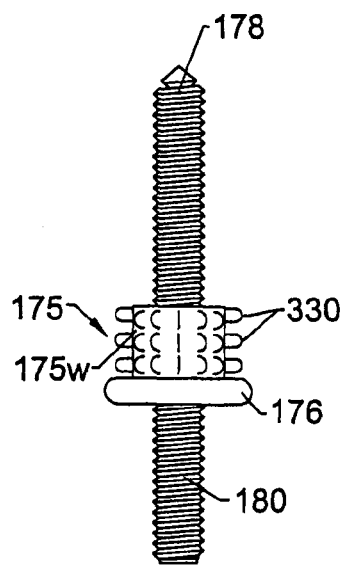 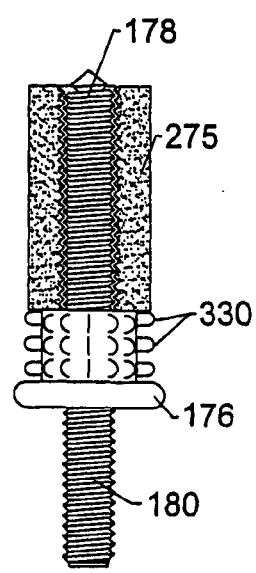
FIG. 16A. FIG. 16B. FIG. 16C.
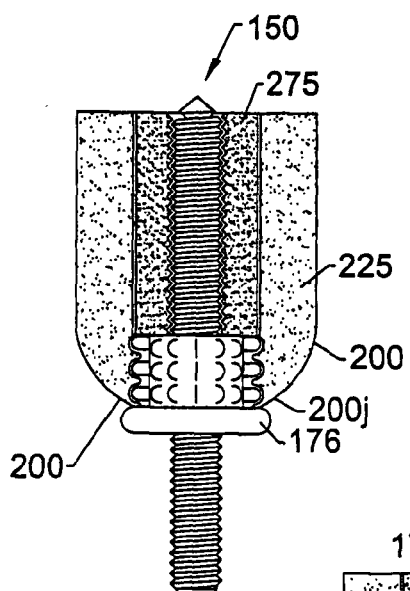 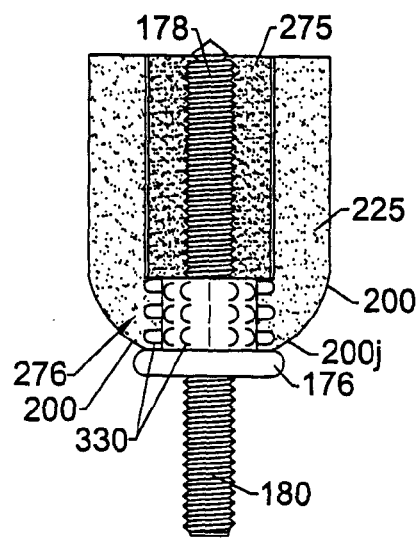
FIG. 16D. FIG. 16E.
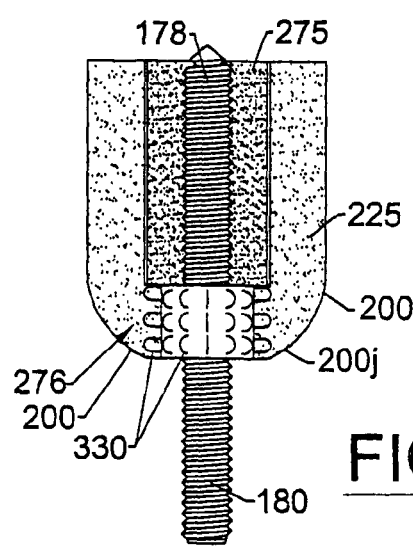
FIG. 16F.

```
┌─────────────────────────────────────────┐
│  RESECT SKIN TO FREE SKIN EDGE FROM     │
│         SUBCUTANEOUS TISSUE             │
│      SUCH THAT SKIN HAS AN OPENING      │
│      WIDTH CORRESPONDING TO THE         │
│           WIDTH OF THE DEVICE.          │
│                  300                    │
└─────────────────────────────────────────┘
                    │
┌─────────────────────────────────────────┐
│  POSITIONING THE PERCUTANEOUS DEVICE    │
│        HAVING A PRIMARY BODY AND A      │
│    MESH COLLAR EXTENDING OUTWARDLY      │
│     THEREFROM SUCH THAT THE MESH        │
│    COLLAR IS LOCATED BETWEEN FREED      │
│      SKIN AND SUBCUTANEOUS TISSUE.      │
│                  310                    │
└─────────────────────────────────────────┘
                    │
┌─────────────────────────────────────────┐
│         POSITIONING THE DEVICE IN       │
│   THE SUBJECT AT A REGION DEFICIENT     │
│            IN ADIPOSE TISSUE.           │
│                  312                    │
└─────────────────────────────────────────┘
```

FIG. 19.

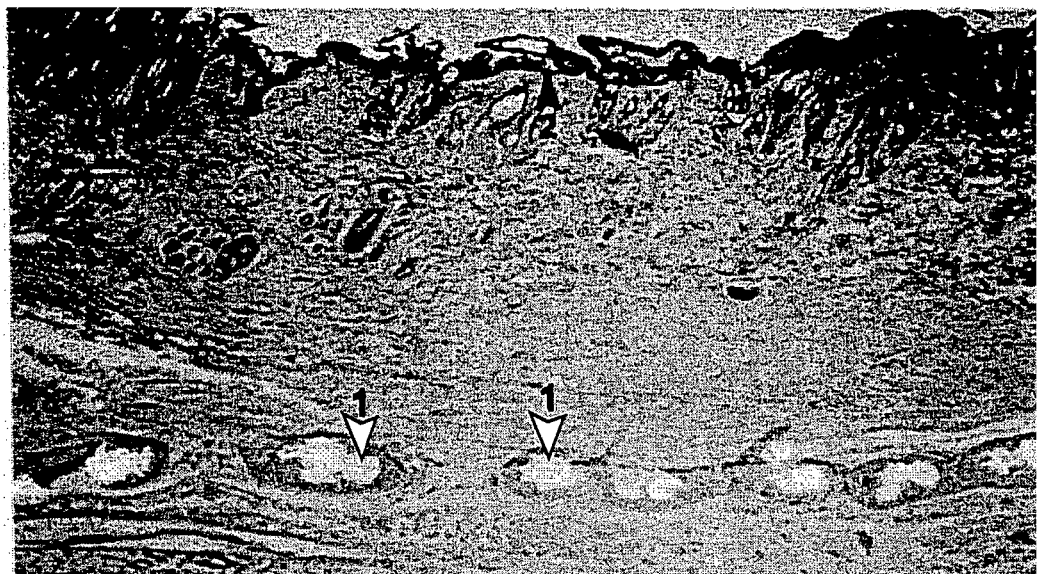
FIG. 20

TISSUE LOCKABLE CONNECTING STRUCTURES

RELATED APPLICATIONS

This application claims the benefit of priority from PCT Application No. US0/32606 filed Nov. 30, 2000 which claimed benefit of priority from U.S Provisional Application Ser. No. 60/244,735 filed Oct. 31, 2000, the contents of which are hereby incorporated by reference as if recited in full herein.

FIELD OF THE INVENTION

The invention relates to tissue locking structures and implantable percutaneous barrier devices for providing a way to enter through the skin of a subject safely and chronically for artificial or foreign objects such as wires, tubing, bars, plates, containers, and also relates to bioconnection structures useful for other devices such as skeletal pins, dental implants, or prostethic devices.

BACKGROUND OF THE INVENTION

Generally stated, skin functions to shield internal tissues from the environment and to protect against infection. Many implantable artificial organs and foreign devices require skin penetration which can disrupt the protective barrier typically provided by the skin under natural conditions. Percutaneous access devices (PADs) permit long-term skin penetration that allows access to and/or a connection between the interior of the body and an external device.

One common problem associated with PADs, implanted on a long-term basis, is that the bio-sealing connection between the skin and the device can be weak and not sufficiently strong to be able to resist detaching or fracturing during the stress introduced onto the skin during normal life activities. Unfortunately, a break in the bio-seal connection can lead to soft tissue infection and other complications. For example, epidermal cells can migrate and skin downgrowth can occur in an attempt to expel the foreign device from the body. Marsupialization may result wherein the skin surrounding the device forms a pocket and spontaneously expels the device. Alternatively, sinus tracts may form when marsupialization is incomplete and/or deep tissue infection may occur.

In the past, many designs for PADs have been proposed. Certain of these devices have used flanges to help hold the device in the body. However, and unfortunately, the configuration or location of the flange typically limited its ability to provide suitable connective assistance. For discussion purposes, disregarding the use of flanges on conventional PADs, the conventional PADs may be divided into two types: a flat connecting structure (FCS); and an anchored connecting structure (ACS). Both FCS and ACS type PADs can produce bio-sealing connections in tissue with bio-adhesive factors present in blood and other body fluids, to help interconnect the device and the tissue. Generally stated, the primary difference between the FCS and the ACS devices is that the FCS has a relatively limited or basic connecting surface area while the ACS has a larger connecting surface area, which can be a rough surface structure. As such, many of the ACS devices are able to form stronger bio-sealing connections than FCS devices. Unfortunately, each of these types of devices may cause infection, skin downgrowth, and other complications. Further, the bio-sealing connections proposed by these conventional PADs may be too weak to maintain the integrity of the bio-sealing connection during normal life activities, particularly when implanted for chronic or long-term indwelling periods of time.

In view of the foregoing, there remains a need for improved infection resistant support structures for securing devices to tissue.

SUMMARY OF THE INVENTION

In certain embodiments, the present invention can provide locked connecting structures (LCS) which engage with the localized tissue and provide improved mechanical connections at a junction layer located between the outer surface of the device and the tissue locking structures mounted thereto. The mechanical connection protects the bio-sealing connection and the intact bio-sealing connection, in turn, inhibits tissue and skin infection, even in long-term indwelling applications. The locked connecting structures can be used for a number of medical applications including on percutaneous access devices. The locked connecting structures are adapted to provide a sufficiently strong bio-connection and with sufficiently strong structural support so as to inhibit the disruption of the bio-sealing connection and enhance the survivability of the bio-sealing connection during normal life activities even during long-term indwelling applications.

The device can include a primary body and a tissue connecting structure. The primary body configuration, size, and shape are typically determined by its intended use for the planned physiological or medical purpose. In certain embodiments, the tissue connecting structure includes a skin level tissue connector. In other embodiments the device can also (or alternatively) include a plurality of tissue connectors which can be positioned at various positions on the device, such as above the skin, at skin level, or as subcutaneous tissue connectors.

In some embodiments, the skin level connector is a thin, semi-rigid mesh, collar which is positioned on the primary body so that the mesh collar can engage with skin (tissue grows therethrough) when positioned in the subject. Typically, the mesh collar will be positioned proximate a top portion of the device. In other embodiments, the tissue connectors can be located adjacent the external surface of the primary body and arranged to extend away from the exterior surface of the primary body. The tissue connectors can be formed on a substrate, which is attached to the external surface of the device or formed directly onto the device body. The tissue connectors may be configured as hooks, loops, rings, or the like with apertures formed therethrough.

In position, groups of cells and capillaries grow through the apertures either in the mesh collar (where used) and/or the tissue structures to form the bioconnection and secure or "lock" the tissue and device together to form a strong mechanical bioconnection capable of maintaining viability.

In certain embodiments, substantially rigid or semi-rigid hooks or rings can also be used as skin connectors (and/or to also extend above the skin level) to allow tissue at the skin level to lock thereto and provide structural support about the bio-connection with the skin.

In some embodiments, a plurality of open ended (or open-sided) rigid or semi-rigid connectors (preferably configured to substantially retain their form or not to collapse in situ) can be positioned about devices which are positioned in the body of a subject on a temporally limited basis (such as during a healing period of a broken bone). The connectors can be configured to lock with the tissue when in position and then to releasably detach from the tissue at a desired removal time. Thus, the connectors are configured to allow tissue to grow about them, in position in the body during the healing period, and to disengage from the localized tissue in a manner which can inhibit tissue damage attributed to removal (and without requiring surgical excision of the connectors).

In some embodiments, the connectors are hooks with open side or end portions (or stated differently, the hook is configured with one free end portion), which are circumferentially arranged about an elongated pin body which can be used to stabilize a bone fracture. To position the pin in the body, the pin can be inserted or rotatably screwed into the bone. To remove, the pin can be rotated in a direction, which dislodges the tissue and frees the tissue to allow it to disengage and release thereat from the open portion of the hook. The pin can then be pulled or rotated out of the bone.

Other embodiments of the present invention further comprise a skin stop collar positioned below and proximate to the mesh collar so that cells may grow in between the two structures providing additional structural stability and support for the device. In some of these embodiments, the subcutaneous tissue connectors may also be used, but are not required.

An additional embodiment of the present invention is a percutaneous locking system. The tissue locking system includes a plurality of bio-tissue connectors (such as rigid or semi-rigid loops, rings, and/or hooks) which dispose about a portion of an external surface selected biocompatible implantable device. The plurality of tissue connectors are sized and configured to allow bundles of cells and associated capillaries to grow therethrough. In certain embodiments, the tissue connectors are attached to the outer surface of the selected implantable device and are formed from a dense mat of polymer fibers.

In certain embodiments, the locking structures or devices of the present invention may be used for providing operational access and/or in vivo structural support for drug delivery systems, implantable medical devices, implantable sensors for detecting physiological parameters (glucose levels, blood pressure, etc. . . . ), load bearing support for prosthetic or artificial limbs, bioelectricity feedback, input, output and/or control for prosthetic or artificial limbs, stabilizing supports for fractures, access ports for fluid delivery paths (to drain fluids from or administer fluids such as insulin to the subject), providing an enclosed connection to deliver air or power to implanted devices or artificial organs such as an artificial heart or pacemaker performing peritoneal dialysis, obtaining blood samples, directing medicines and pharmacological drugs to the patient, in vivo positioning support for implanted artificial corneas, and the like.

Advantageously, certain embodiments of the devices of the present invention may be implanted in areas deficient in subcutaneous adipose tissue. Adipose tissue typically enables the fixation of the subcutaneous connector in place at the implantation site. Adipose tissue, for many devices, is thicker than the length (thickness) of primary functional body or bioconnection downshift may occur between the skin and the device. Bioconnection downshift is differentiated from skin down growth in a number of ways. Specifically, a tight seal between the device and the skin is maintained with bioconnection downshift, and infection is not typically associated with bioconnection downshift.

One aspect of the present invention is a percutaneous barrier or access device configured for implantation into a subject to provide subcutaneous access therethrough. The device includes a primary body having opposing top and bottom portions, each with a respective outer surface, and at least one sidewall extending therebetween. In position in a subject, the primary body bottom portion resides within the subject and the bottom portion outer surface faces into the subject. The device also includes an outwardly extending mesh collar attached to said primary body such that said mesh collar is positioned intermediate the top and bottom portions and extends outwardly from the at least one sidewall a first distance. In position in the subject, the mesh collar is configured to engage with the skin of a subject.

In some embodiments, a skin stop collar can be attached to the primary body such that the skin stop collar is proximate to and beneath the mesh collar. Tissue connectors can be positioned either or both above and below the mesh collar.

Another aspect of the present invention is a skeletal limb extension device for providing support for a prosthesis device. The device includes an elongated extension member adapted configured to attach to the bone of a subject such that, in position, the elongated extension member resides inside the body of the subject. The device also includes a tissue connector member attached to the elongated extension member, said tissue connector member having opposing distal and proximal portions at a sidewall portion extending therebetween, the distal portion configured to reside inside the subject and at least the outer surface of said proximal portion configured to extend external of the subject above and proximate the normal level of the skin. The tissue connector member includes a plurality of tissue connectors extending outwardly from the sidewall and configured to engage with subcutaneous tissue in the subject. The device also includes a prosthesis attachment member attached to the tissue connector member in a direction opposing the elongated extension member such that the prosthesis attachment member extends outwardly from the subject. The skin of the subject attaches to the upper portion of the perimeter of the sidewall to define a (bioconnection) sealing junction about the device. The skeletal extension device defines a load path through the elongated extension member, the tissue connector, and the prosthesis attachment member in a manner which inhibits and/or avoids contact with skin and subcutaneous tissue.

An additional aspect of the present invention is a method of attaching a prosthetic device, comprising the steps of: (a) inserting an elongated extension member into a selected bone of a subject; (b) attaching a tissue connector member to the elongated extension member; and (c) positioning the tissue connector member in the subject such that it resides below the bone and elongated member in a load path which is substantially devoid of subcutaneous tissue.

Another aspect of the present invention is a method of implanting an access device having a semi-rigid collar adapted to engage with the skin of a subject. The method comprises the steps of: (a) introducing an opening in the skin of a subject; and (b) positioning the device into the opening of the subject such that the mesh collar resides below but proximate the skin of the subject so that, over time, the skin engages with the mesh collar and defines a bioconnection proximate the perimeter of the device about the outer surface of the skin to close the opening of the introducing step.

Another aspect of the present invention is a method of providing a structurally supported bioconnection for a device positioned to extend through the skin. The method includes the steps of: (a) implanting a device having a perimeter with a plurality of outwardly extending tissue connectors mounted thereon, each tissue connector defining an aperture sized in width at about 0.2–4 mm; and (b)

growing proximately located tissue into proximately located tissue connectors such that the tissue connectors engage with the tissue and provide structural support for the bioconnection.

Yet another aspect of the invention is a method of locking a foreign object into a biological subject. The foreign object includes a plurality of outwardly extending tissue connectors connected to the outer perimeter of the foreign object. Each of the tissue connectors has an aperture formed therein. The method comprises the step of implanting the object into a biological subject such that localized tissue grows into the apertures in the tissue connectors to provide a bioconnection which can provide structural support for the object in the biological subject. The apertures have an opening gap size of between about 0.2 mm–5 mm. The object is adapted to reside in the biological subject for at least 6–12 months.

In certain embodiments, the tissue connectors are arranged on a portion of the perimeter of the object in a quantity of between about 50–100 per $cm^2$. The foreign object can be or provide support for a dental implant, an artificial cornea, a percutaneous access device, and the like.

Other embodiments of the invention provide a pin for providing structural support for treatment of a bone condition. The pin can include an elongated member having a perimeter configured for positioning into a biological subject; and a plurality of connectors attached to and extending outwardly from a portion of the perimeter of the elongated member. The connectors can have a body shape with a discontinuous open portion adapted to engage with biomaterial in situ. When the connectors are moved in a predetermined direction, the localized tissue disengages therefrom.

The devices and methods of the present invention can provide improved structural (mechanical) support for the device and inhibit damage due to stresses or loads introduced onto the bio-sealing surface as well as to provide mechanical support at the junction layer which is arranged about the implanted portion of the body of the device during use.

The foregoing and other objects and aspects of the present invention are explained in detail in the specification set forth below.

BRIEF DESCRIPTION OF THE DRAWINGS

FIG. 2G illustrates that after a healing period, the localized tissue is effectively biosealed to the external surface of the device and mechanically locked to the device.

FIGS. 3A–C illustrate the in situ formation of a tissue locking or connecting structure according to embodiments of the present invention. As shown, FIG. 3A is a partial perspective view of a substrate sheet holding a plurality of ring tissue connective structures thereon and FIGS. 3B and 3C illustrate the tissue connecting structures with the tissue forming a bio-connection and mechanical attachment to the tissue connectors of FIG. 3A as they may appear in the body after an initial healing period. FIG. 3B illustrates the device remains in place with the bioseal intact during exposure to light activity or stress and FIG. 3C illustrates the same even during or after exposure to significant and generally abnormal activity or stress.

FIGS. 4A–4C illustrate another tissue connecting structure according to another embodiment of the present invention. FIG. 4A is a partial perspective view of the tissue connecting or locking structures held on a substrate sheet. This embodiment illustrates that the tissue connecting structure can be an open end or hook configuration. FIGS. 4B and 4C illustrate the bioseal and mechanical connection between the device (i.e, at the tissue connectors) and tissue after or during exposure to light activity or stress (FIG. 4B). FIG. 4C illustrates that the tissue connectors can be removed or disengaged from the localized tissue without requiring surgical cutting thereabout.

FIG. 5A is a partial top view of a device with a single row of tissue connecting structure thereon according to embodiments of the present invention.

FIG. 5B is a partial top view of the embodiment of FIG. 5A, modified to include a plurality of rows of tissue connecting structures to form a mesh collar.

FIG. 5C is a partial top view of an embodiment of the present invention, which is similar to FIG. 5B. This embodiment shows that the mesh collar may be woven with weft and warp yarns.

FIGS. 5D–5G are side views of the mesh collar shown in FIG. 5C. FIG. 5E illustrates the device in the subject positioned between soft tissue, after surgical placement. FIG. 5F illustrates that the soft tissue locks to the mesh collar after healing. FIG. 5G illustrates the bio-seal junction as it is anticipated it will be after exposure to reasonable life activity (stress), the mechanical connections provided by the mesh collar being able to maintain the integrity of the bioseal (the seal between the tissue and the body of the device).

FIG. 6A is a front sectional view of the device before implantation. FIG. 6B is a partial cutaway view of the device of FIG. 6A after implantation. FIG. 6C shows the implanted device of FIG. 6B after the tissues are healed.

FIG. 7A illustrates the device before implantation, FIG. 7B illustrates the device after implantation, and FIG. 7C illustrates the device after the tissues are healed.

FIG. 8A illustrates the device before implantation, FIG. 8B illustrates the device after implantation, and FIG. 8C illustrates the device after the issues have healed.

FIG. 13B illustrates that the cornea can be partially or fully resected to split the rest cornea into two layers (or to free the conjunctiva from the sclera) and the artificial cornea can be positioned with the tissue connective structure (which may be a mesh collar) positioned intermediate the split layers and the eye tissue can then be sutured to the root of the mesh collar. FIG. 13E illustrates how the artificial cornea may appear after healing is complete.

FIG. 14A is an enlarged side view of an elongated pin or bar with outwardly extending tissue connectors positioned thereon according to embodiments of the present invention.

FIG. 14B is a section view of the tissue connector portion of the pin shown in FIG. 14A.

FIG. 14C is a side view of the pin or bar of FIG. 14A, which illustrates the pin or bar of FIG. 14A positioned in the bone of a subject and extending out through soft tissue and then skin.

FIG. 14C$_1$ is a section view of the tissue connectors of FIG. 14C illustrating the tissue has not yet engaged therewith at initial placement of the in the subject.

FIG. 14D is a side view of the pin or bar of FIG. 14A, illustrating the tissue has migrated and formed a locked connection with the tissue connectors.

FIG. 14D$_1$ is a section view of the tissue connectors of FIG. 14D illustrating the tissue has engaged therewith after a healing period.

FIG. 14E is an enlarged section view of the tissue connectors in the subject, as shown in FIG. 14D$_1$, illustrating the static configuration of the connectors in the body (with all of the hooks arranged to face the same direction) according to certain embodiments of the present invention.

FIG. 14F is a greatly enlarged partial view of the tissue connectors shown in FIG. 14E.

FIG. 14G shows the tissue connectors of FIG. 14E in a dynamic state, as the pin or bar is rotated to force the locked localized tissue to slip of when the direction of movement of the pin matches the face of the hook (the open region facing the rear for clockwise rotation) according to embodiments of the present invention.

FIG. 14F is a greatly enlarged partial view of the tissue connectors shown in FIG. 14G, illustrating the tissue releasing from the hook connector as the pin is moved in a direction corresponding to the continuous portion of the hook, according to embodiments of the present invention.

FIG. 16A is a front view of a skeletal structure prepared for implantation of an extension member for connecting an artificial limb or prosthesis according to embodiments of the present invention.

FIG. 16B is a front view of a skeletal extension device according to embodiments of the present invention.

FIG. 16C is a front view of the device shown in FIG. 16B inserted into the bone structure of FIG. 16A according to embodiments of the present invention.

FIG. 16D is a front view of the device of FIG. 16C illustrating the skin and subcutaneous tissue surrounding the device according to embodiments of the present invention.

FIG. 16E is a front view of the device shown in FIG. 16D illustrating the bioconnection of the tissue and skin with the device according to embodiments of the present invention.

FIG. 16F is a front view of a device similar to that shown in FIG. 16E, illustrating an alternate embodiment of device according to the present invention.

FIG. 19 is a block diagram of a method for providing percutaneous access to a subject according to embodiments of the present invention.

FIGS. 20A and 20B are enlarged microscopic image of the cross-section of a skin sample taken adjacent a device used in a study (at 16 weeks post implantation).

FIG. 20A, the top image, is at 50× and, FIG. 20B, the bottom image is at 250×. The cross section of skin demonstrates the orientation of the mesh fibers in the deep dermis (associated with the identifier "1") in the images. The upper image indicates that healing is complete, normal skin architecture has been preserved and little residual inflammation is present. The epidermis ("2") is at the top of the section. The cross section of deep dermis adjacent the device demonstrates two mesh fibers ("1") and intervening tissue. The fibers are surrounded by occasional mononuclear infiltrates and a thin band of fibrous tissue ("3"). Multiple cross sections of capillaries can be found surrounding the mesh fibers ("4"). A collection of adipocytes is between the mesh fibers.

DESCRIPTION OF PREFERRED EMBODIMENTS

Figure 1A:
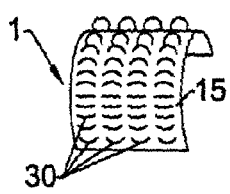
FIG. 1A is a greatly enlarged partial perspective view of a tissue-engaging locked or secure bio-connection structure which can be mounted onto tissue engaging surfaces of desired implantable medical objects according to certain embodiments of the present invention.

The present invention will now be described more fully hereinafter with reference to the accompanying figures, in which preferred embodiments of the invention are shown. This invention may, however, be embodied in many different forms and should not be construed as limited to the embodiments set forth herein. Like numbers refer to like elements throughout. In the figures, layers, regions, or components may be exaggerated for clarity.

The methods and devices of the present invention include improved bioconnection structures which can promote the success of long-term indwelling devices in the body. The bioconnection structures can be important to provide access to (and optimal management of) internal tissue, to allow the treatment of many diseases by the use of long term implantable devices (such as the delivery or insulin or drugs for the treatment (or prevention of the onset of) diabetes), or to provide durable and reliable support or infection resistant bioseals access for artificial organs or prosthetic devices including artificial limbs. "Long term" means that the device can remain implanted in the subject for about 3–6 months, 6–12 months, 1–2 years or even longer.

In certain embodiments, the present invention can provide locked connecting structures (LCS) which engage with the localized tissue and provide improved mechanical connections at a junction layer located between the outer surface of the device and the tissue locking structures mounted thereto. The mechanical connection can protect the bio-sealing connection from stresses imparted thereto during normal life activities, maintain the integrity of the bio-sealing connection (substantially intact). In turn, the maintenance of the bioseal connection between the device and the localized tissue can inhibit tissue and skin infection, even in long-term indwelling applications. The locked connecting structures can be used for a number of medical applications to help secure the device in localized tissue and promote stronger bioseals thereat. The locked connecting structures can be used, for example, on implantable percutaneous access devices. Thus, generally described, the locked connecting structures of the present invention are adapted to provide a sufficiently strong bio-sealing connection and with sufficiently strong structural support so as to inhibit the disruption of the bio-sealing connection and enhance the survivability of the bio-sealing connection during normal life activities even during long-term indwelling applications.

In position, groups of cells and capillaries grow through the locked connecting structures (through apertures either in the mesh collar (where used) and/or the tissue connector structures) to form the bioconnection and secure or "lock" the tissue and device together to form a strong bioconnection capable of maintaining viability. As such, the mechanical or bioconnections between the device and the localized tissue provided by tissue locking structures of the present invention (including a mesh collar and/or tissue connectors) positioned about perimeter surfaces of the implantable device which defines a sealing junction(s) which allows the proximately located biomaterial (such as localized tissue and capillaries) to grow into the apertures provided by the tissue locking structures and thereby "lock" into position to provide mechanical connections between the device and localized tissue. In some embodiments, the implantable device may be able to float or move together with the skin to inhibit impairment of the bioseal during normal life activities.

Figure 1B:
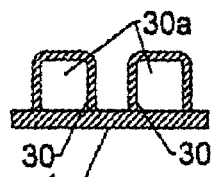
FIGS. 1B–1D are greatly enlarged section side views of embodiments of the embodiment shown in FIG. 1A illustrating the tissue moving to form the bio-seal connection at the external surface of the device and to engage with (or lock with) the tissue connectors at a localized bio-junction layer according to embodiments of the present invention.
Figure 1C:
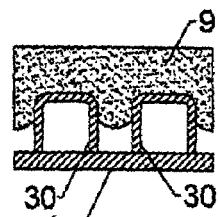
Figure 1D:
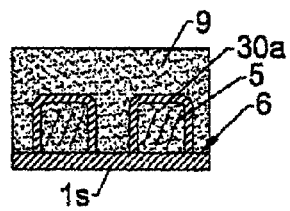

Turning now to FIG. 1A, one embodiment of a tissue lockable connecting structure 1 is shown. As shown, the tissue lockable connecting structure 1 includes a plurality of tissue connectors 30 held on a substrate sheet 1s, which can be attached to the external surface of a device or a primary implantable body. As shown in FIGS. 1B–1D, in position in the subject, the plurality of tissue connectors 30 extend away from the device and into the localized soft tissue 9. In this embodiment, the tissue connectors 30 are small loops or rings which can be spaced apart a distance of about 0.2–4 mm, and in some embodiments, can be about 0.4–2 mm. Although shown as arranged in four linear rows, more or less numbers may be employed (such as a single row), and the rings may be arranged in a non-linear or asymmetrical manner. In some embodiments, the width or diameter (and height or length) of the tissue connector 30 elements or units (shown as a ring in FIG. 1A) can be about 0.2–4 mm, and typically is about 0.4–2 mm. The aperture 30a (or air space gap) defined by the body of the tissue connector 30 can be from bout 0.04–16 mm$^2$, and may be more typically sized from about 0.16–4 mm$^2$. The tissue connectors 30 are preferably configured to resist deformation in the body (i.e., is sufficiently rigid so as to be able to retain its shape in situ). The tissue connectors 30 will be described further below.

FIG. 1C illustrates the that localized soft tissue 9 has not yet engaged with the tissue connectors 30 (such as it may appear at the time of initial implantation). FIG. 1D illustrates the tissue lockable connecting structure 1 in the body after healing. As shown, the soft tissue 9 has entered the apertures 30a and attached to the external surface of the substrate sheet 1s to define the bioseal connection 6 thereat. In position, the localized tissue enters the apertures 30a and acts to substantially encase and fill the aperture of gap of the tissue connector as well as the spaces defined between adjacent tissue connectors 30 to lock 5 the associated implanted object and the tissue together. Although shown as mounted to the substrate sheet 1s, the tissue connectors 30 may be formed directly onto the external surface of the desired implantable object or device.

Figure 2A:
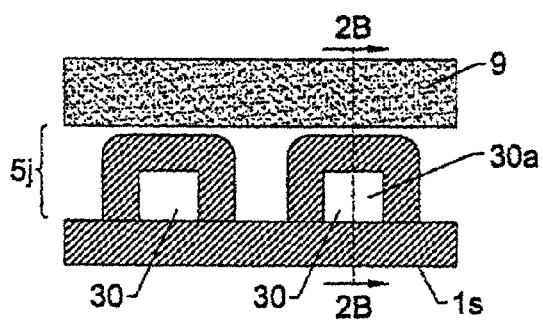
FIGS. 2A–2G are greatly enlarged schematic illustrations of embodiments of the present invention illustrating the tissue molding, forming, or growing about a bio-junction layer defined between the exterior surface or wall of an implantable device and the outermost perimeter portion of the tissue connective structures to provide a structural or mechanical connection for the device with tissue in the body of the subject.
Figure 2B:
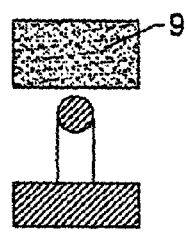
Figure 2C:
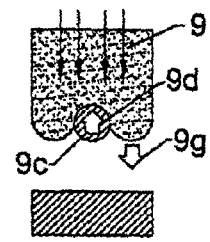
Figure 2D:
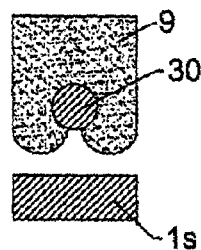
Figure 2E:
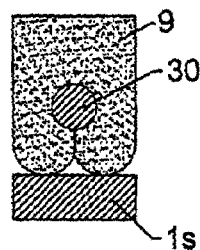
Figure 2F:
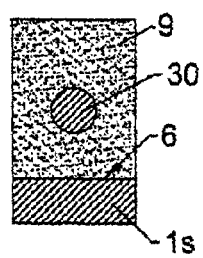
Figure 2G:
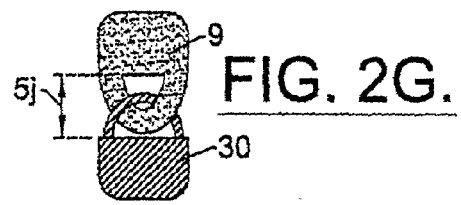

FIGS. 2A–2G illustrate the tissue connectors 30 as closed rings and the figures illustrate the progression of the healing soft tissue 9 to the junction layer 5j extending between the perimeter of the tissue connectors 30 and the external surface of the substrate sheet 1s or the underlying outer wall of the device (11w, FIGS. 6, 7, 8, 9, 14 et seq.). The aligned plurality of arrows in FIG. 2C are meant to illustrate the stress direction attributed to tissue elasticity and the use of protective sutures to help stabilize the device during initial healing. The localized tissue 9 may experience a slow cutting effect as shown by arrow 9c, and the arrow noted by reference number 9g illustrates the growth direction of the cells. A degeneration zone 9d may extend about the external perimeter of the tissue connector 30. In position, i.e., after initial placement, the localized tissue 9 migrates to merge together into and about the boundary of the tissue connectors and the device outer wall (or substrate sheet 1s outer wall). FIG. 2G illustrates that the locked connective structure provided by the tissue connectors 30 and the localized tissue 9 can be described as a locked chain.

FIGS. 3A–C illustrate a similar tissue progression about tissue connectors 30, and that the tissue connectors can provide a sufficiently strong mechanical bond so as to maintain the integrity of the tissue along the device body (about a junction layer 5j) even when exposed to forces as noted by the arrow and the letter "F" in FIG. 3C. The connectors 30 are shown with a closed loop or ring with an open center and as separated by a gap space indicated by "sp" which, as described above, in some embodiments, can be on the order of or less than the size of the apertures 30a.

FIGS. 4A–4C illustrate an alternate embodiment of the tissue connectors 30'. As shown, the tissue connector 30' has a hook with an aperture 30a' formed therein. The hook 30a can also be described as having a discontinuous perimeter side or end portion, or being configured with a free end (unlike the two captured ends of the loop or ring embodiment above). In some embodiments, the hook 30a may be configured with a single long leg and the short leg can be omitted. FIG. 4B, illustrates that for significant loading or stress, the hooks may yield. In addition, the hooks 30' may be able to be disengaged from the localized tissue 9 without requiring a physician to cut the localized tissue to remove it from the device (pulling away to dislodge the tissue with forceps or the like may be sufficient and can reduce tissue damage to the localized tissue upon removal). This configuration may be particularly suitable for shorter term (i.e., less than a year) indwelling applications.

FIGS. 5A–5C are partial top views of a locked tissue connecting structure 1" which can be arranged about a top portion of a suitable implantable device (in this embodiment, preferably located so that it resides just under the skin at skin level). FIG. 5A illustrates a thin single row of tissue connectors 30. FIGS. 5B–5C illustrate a plurality of adjoined outwardly extending rows defining a thin mesh collar 12 of suitably sized apertures 12a to define the tissue connectors. FIG. 5C shows that the mesh collar 12 may be formed from interwoven warp and weft fibers 12L, 12U. The mesh collar 12 will be discussed further below. FIGS. 5D–5G schematically illustrate the migration of the localized tissue 9 about the mesh collar 12 and into the apertures 12a thereof and that the mechanical connection formed thereby is formed so as to inhibit or resist breakage at the bioseal 6 when exposed to forces or stress associated with normal life activities ("F").

Figure 6A:
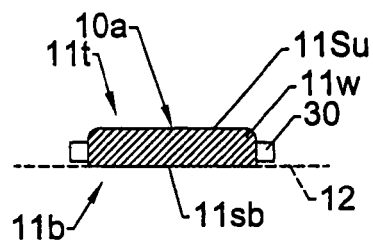
FIGS. 6A–C are schematic illustrations of an implantable device which may be particularly suitable for seating in subcutaneous tissue according to embodiments of the present invention.
Figure 6B:
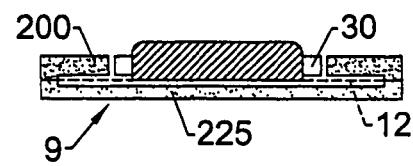
Figure 6C:
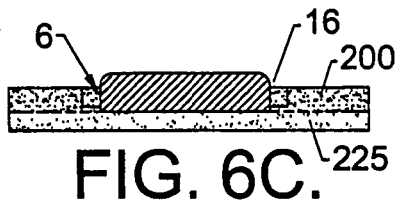

FIGS. 6A–6C illustrate one embodiment of a percutaneous barrier or access device 10a which may be particularly suitable for seating in subcutaneous tissue 225 as shown in FIGS. 6B and 6C. The device 10a includes a primary body 11. The primary body 11 may comprise rigid, conformable, or flexible materials such as metals, elastomeric, or fabric materials. The outer surface of the primary body can be formed from or coated with a non-porous biocompatible material. As shown, the primary body 11 includes a top portion 11t and an opposing bottom portion 11b, each with a primary outer or external surface 11Su, 11Sb. The primary body 11 also includes at least one wall 11w extending between the top and bottom portions 11t, 11b. For ease of discussion, the primary body 11 is shown primarily throughout as a disc-like or cylindrical body; however, the present invention is not limited thereto. The shape of the primary body 11 may vary depending on the function and/or on the application. For circular, spherical, frustoconical, or other primary body shapes the at least one wall 11w can be one contiguous wall. For elliptical, rectangular, pyramidal, square, or other shapes, the primary body 11 may include a plurality of attached or merging walls defining the perimeter of the primary body 11 (not shown).

As shown in FIG. 6A, the device 10a may be a thin medical object (which can be seated in regions deficient in adipose tissue). The device 10a includes a thin mesh collar 12 which extends outwardly from the perimeter of the primary body 11 and a plurality of tissue connectors 30 arranged above the mesh collar 12. The mesh collar 12 is adapted to contact and underlie the skin layer 200 and can be positioned between the skin 200 and the subcutaneous tissue 225. The tissue connectors 30 are arranged on the primary body wall 11w to engage with skin tissue. As such, in this embodiment, the localized tissue 9 may include both skin and subcutaneous tissue 200, 225 as the skin and subcutaneous tissue can grow together through the apertures 12a of the mesh collar 12.

Figure 7A:
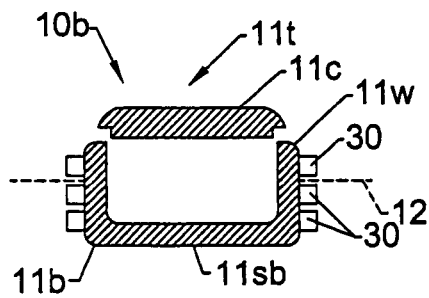
FIGS. 7A–C are schematic illustrations of another implantable device which may be particularly suitable for seating on subcutaneous tissue according to the present invention.
Figure 7B:
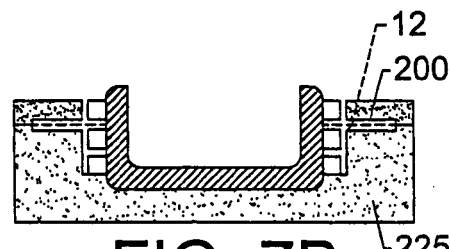
Figure 7C:
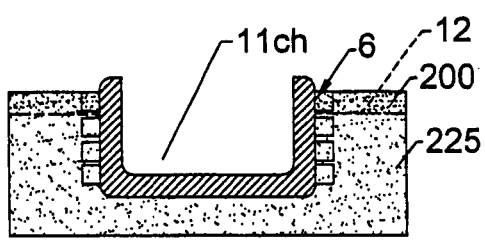

FIGS. 7A–7C illustrate another embodiment of a percutaneous access device 10b, which may be particularly suitable for seating on or over subcutaneous tissue 225. This device is also includes both a mesh collar 12 and tissue connectors 30 positioned about the outer wall of the device 11w. As shown, the tissue connectors 30 may be positioned both over and under the mesh collar 12. The tissue connectors 30 positioned below the mesh collar 12 are adapted to engage with subcutaneous tissue 225 and at least some of those positioned above, adapted to engage with skin tissue. The device 10b can include a removable cover 11c and may include an enclosed bottom (defining an enclosed holding chamber 11ch). Alternatively, the device may include an aperture or passage in the bottom as needed by the particular application.

Figure 8A:
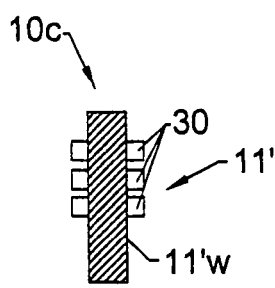
FIGS. 8A–8C are schematic illustrations of yet another implantable device which may be particularly suitable for mounting adjacent bone according to embodiments of the present invention.
Figure 8B:
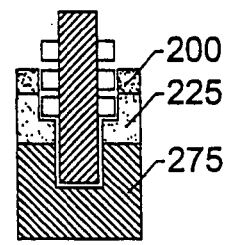
Figure 8C:
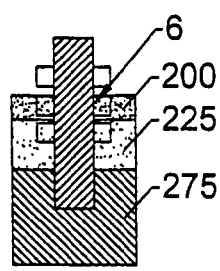

FIGS. 8A–C illustrate another device 10c, which may be suitable for implantation adjacent bone and subcutaneous tissue. For example, such a device may be used to attach portions or fragments of bones together (or otherwise mount to or engage with skeletal bone). This device 10c can be a bar or pin, i.e., an elongated body which employs a series of tissue connectors 30 extending over a portion of the perimeter of the pin body 11'. As shown in FIGS. 8B and C, the pin or bar 11' is fixed into bone 275 and extends through bone 275, subcutaneous tissue 225, and skin 200. In position, some of the tissue connectors 30 may be positioned such that they reside both above and below the normal level of the skin when the device is in the body. Those below can be both at the skin level (defining skin connectors) and at the subcutaneous level (for subcutaneous connectors). Those above the normal skin level at the time of implantation, allow the skin to shift up (or down) on the tissue connectors 30 without breaking (or inhibiting the disruption of) the bio-seal 6. This movement can occur naturally over time as the subject may gain or lose weight and the like.

Figure 9A:
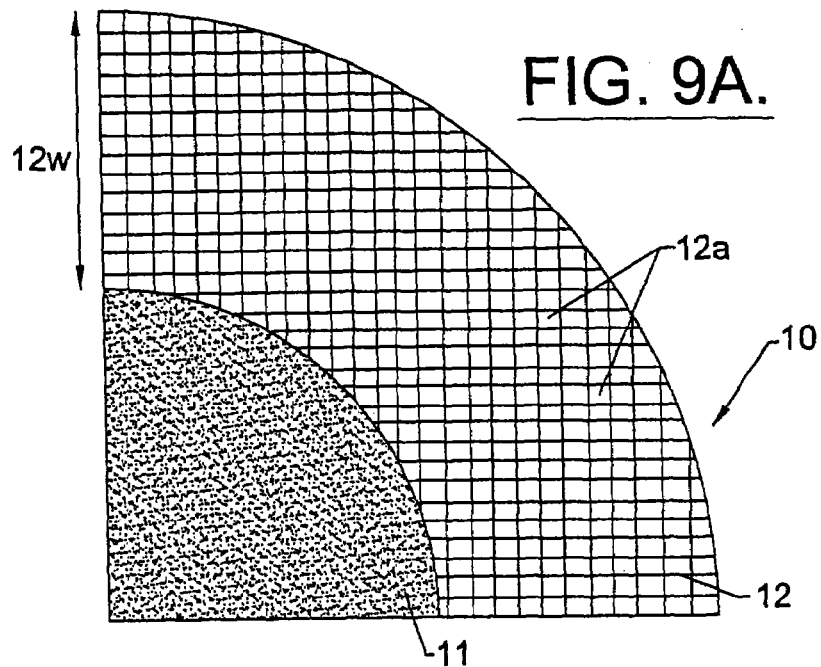
FIG. 9A is a partial top view of a device of an embodiment of the present invention.
Figure 9B:
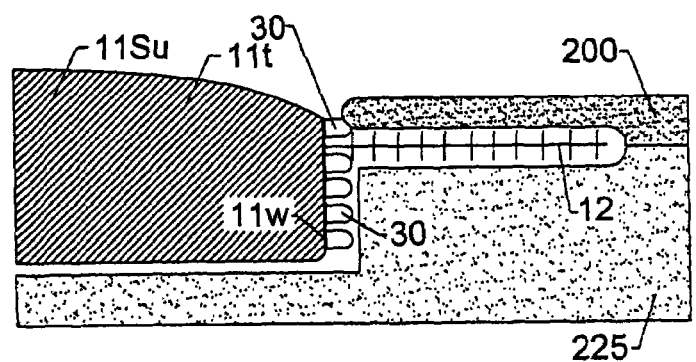
FIG. 9B is a partial side view of the device shown in FIG. 9A during the initial placement period in the subject.
Figure 9C:
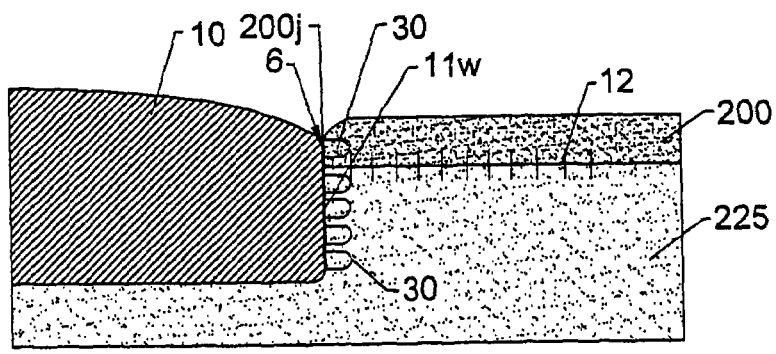
FIG. 9C is a partial side view of the device shown in FIG. 9A in position in the subject after a healing period according to embodiments the present invention.

As shown in FIGS. 9A–D, the mesh collar 12 is attached to the primary body 11 such that, in position in the subject, the mesh collar 12 is located just under the skin 200 (i.e., the dermis/epidermis). That is, the mesh collar 12, in position, is located such that it is underneath the skin layer and so that the upper surface 13 abuts the skin 200. After an initial healing period, as shown in FIG. 9C, the skin 200 grows over and attaches to the underlying mesh collar 12 and grows to close the junction 200j between the device body 11 and the skin 200 (defining a part of the bioseal line or junction 6). Thus, the skin 200, the top portion of the walls 11t, and the upper surface of the device 11Su provide a sealed protective barrier from the environment.

The apertures 12a in the mesh collar 12a can be sized and configured so as to allow capillaries to grow through the thickness of the mesh collar 12. The apertures 12a in the mesh collar 12 can be configured to so that a sufficient supply of blood can be provided in the skin and tissue proximate the implanted device 10. The mesh collar 12 can be sized with a skirt width 12w sufficient to provide a distributed force surface which can help protect the sealing line 200j from undesirable external forces which may be introduced to local skin. The mesh collar 12 can have a skirt area proportional to and/or corresponding to the size and weight of the primary body 11 and/or the functional components held therein. In certain embodiments, the device 10 can be configured without the use of (devoid of) subcutaneous flanges.

The mesh collar 12 can be oriented to extend "laterally" when the device provides a longitudinally oriented access port or "longitudinally" when the device 10 is oriented in the subject to provide a lateral access port 11p. However, the device 10 can be otherwise oriented as the desired location and functional application demands. As shown in FIGS. 6–10, the primary body 11 of the device 10 is substantially cylindrical or disc like and the mesh collar 12 is securely attached to the outer wall of the primary body 11 such that the mesh collar 12 is attached about the circumference thereof and radially extends outwardly a distance therefrom continuously about the external wall of the primary body 11.

FIGS. 5D, 6A, 7A, 9–11, illustrate that the mesh collar 12 can be a thin substantially planar or flat structure which is securely attached to and extends outwardly from the outer circumference of the primary body 11. The mesh collar 12 may provide increased structural stability, force distribution, and loading balance when the device 10 is properly healed and held in position in the subject. Although the mesh collar 12 is shown as a constant diameter skirt with a continuous substantially planar, thin (low profile) body, the mesh collar 12 may be otherwise configured. For example, the outer perimeter edge portion 12p of the mesh collar 12 may be curvilinear or wavelike (not shown).

The mesh collar 12 can be semi-rigid or resiliently configured so that it has sufficient structural rigidity to allow the collar to provide the desired structural reinforcement and attachment in the body and yet sufficiently resilient to be able to substantially conform to the contour of the body about the skin layer of the implant site. In certain embodiments, the mesh collar 12 is sufficiently rigid so as to be able to substantially retain its form (or not to collapse) both ex vivo and in situ. The mesh collar 12 can be formed of resilient and/or thin layer or layers materials which are biocompatible and/or which can be coated with a biocompatible material. In certain embodiments, the mesh collar 12 may be an elastomeric or polymer material such as, but not limited to, NYLON, PVC (polyvinylchloride), PTFE (polytetrafluoroetheylene), and polyurethane. In some embodiments, the mesh collar 12 can be formed from a polymer screen.

The mesh collar 12 can be configured to provide a series of symmetrically configured and sized apertures 12a as shown in FIG. 5C. Alternatively, the apertures 12a can be irregularly sized and spaced (not shown). As noted above, the apertures 12a can be sized to allow tissue to grow through the collar 12 in a manner, which can allow a sufficient supply of blood to reach tissue in this region. The tissue connection provided by the mesh collar 12 can promote a long-term strong, stable bioconnection in a manner, which can inhibit one or more of bioboundary damage, skin downgrowth, or tissue infection. In certain embodiments, the apertures 12a can be configured and sized with an area of between about 0.04–16 $mm^2$, and preferably from about 0.10 $mm^2$ to about 10 $mm^2$, and more preferably in the range of between about 0.5 $mm^2$–5 $mm^2$. The mesh collar 12 can be formed in a number of suitable ways such as by molding, weaving, stamping, and extruding. The mesh collar 12 can be fixed to the outside wall of the primary body 11 such as via adhesives, bonding, or other chemical or mechanical attachment means. In certain embodiments, the mesh collar 12 can be configured with a mesh density (i.e., number of apertures per area) of between about 10–500 apertures/$cm^2$ and preferably from about 30–150 apertures/$cm^2$.

In certain embodiments, the mesh collar 12 can be formed from polymer screen or a woven polyester net formed with about 10–500, and preferably about 50–200 apertures/$cm^2$ 12a. The diameter of the fibers used to form the mesh collar can be from about 0.05–0.2 mm (to define a corresponding collar thickness). In some embodiments, warp and weft fibers can be interwoven and each can have a diameter in the range of about 0.2 mm. The mesh of the collar 12 can be structured so that the warp and weft yarns are substantially fixed relative to each other and define a substantially fixed pore (aperture) size of about 1 $mm^2$. In the embodiment shown in FIG. 11A, the inner edge portion of the mesh collar 12 can be bound by a silk thread and adhesively connected (with silicon glue) to the side surface of the primary body wall 11 proximate the top edge portion 11t of the primary body 11 (shown as proximate the dome 11d in FIG. 11B). Other attachment means can be used to secure the mesh collar 12 to the device body 10. Indeed, the mesh collar may be formed directly onto the device body in lieu of a substrate sheet as noted above. In certain embodiments, the mesh collar 12 can have a thickness, which is in the range of about 0.05–1 mm, and preferably from about 0.10 mm–0.3 mm. In addition, in some embodiments, the mesh collar 12 may have a skirt width (designated "12w" in FIG. 9A) of from about 0.5–2 cm (which may be particularly suitable for primary bodies sized at about 2-3 cm across about the access region in the skin). That is, the device 10 may have a top portion which extends through and above the skin surface which is one shape and size (typically a relatively smaller size) and a different size/shape for the bottom (which is typically the same or larger, see e.g., FIG. 18B).

For the embodiment shown in FIG. 11A, the mesh collar 12 can be about 0.8–1.0 cm wide and the diameter of the opening of the primary body 11 can be about 2.3–2.7 cm. The mesh collar 12 may be provided in a set of different widths, which corresponds to the planned use, size of the subject, and/or implant site as desired. In some embodiments, the width may be selected such that it is in proportion to the width of the primary body at the skin access region. For example, the collar 12 may have a width that is less than the width of the device (at least the part of the device about the opening at the skin), and typically the width of the collar 12 can be sized such that it is less than about 0.3–0.75 times the width of the device thereat.

FIGS. 6–10 illustrate that certain embodiments of the device 10 may include a plurality of tissue connectors 30 either alone or in combination with the mesh collar 12 described herein (see also FIGS. 1–5 and FIGS. 14–16). In FIGS. 7 and 9, the tissue connectors 30 are subcutaneous and can be attached to and extend outwardly from the wall 11w of the primary body. As shown, the tissue connectors 30 are located below the mesh collar 12. Typically, the connectors 30 extend outward from the primary body a shorter distance than the mesh collar 12. The tissue connectors 30 have one or more apertures or openings 30a formed therein. The apertures 30a can be sized to allow tissue to grow into and through the apertures of the tissue connectors 30 in the subject. In certain embodiments, the apertures 30a are sized in the range of between about 0.2–4 mm. In some embodiments the apertures 30a can be from about 0.25–3 mm, and preferably in the range of about 0.4–2 mm and more preferably from about 1–2 mm. The size of the aperture 30a can be such that cells and accompanying capillaries can go through the gap provided by the aperture and approach a junction layer at the perimeter surface of the device. In addition, the aperture 30a can be sized and configured so as to bunch cells together to lock them with the tissue connectors 30 and enhance the mechanical bonding strength thereat which may also provide improved protection for the bioconnection at the skin surface. The tissue connectors 30 can be adapted to engage with different tissues or biomaterials, depending on the implant site or application. For example, the tissue connectors 30 can be configured to engage with desired localized tissue including soft or hard tissue, such as, but not limited to, subcutaneous tissue, epidermal/dermal or skin, muscle, organs, bone, bone marrow, epiphys, cartilage, tendons, mucous membranes, and the like.

Figure 9D:
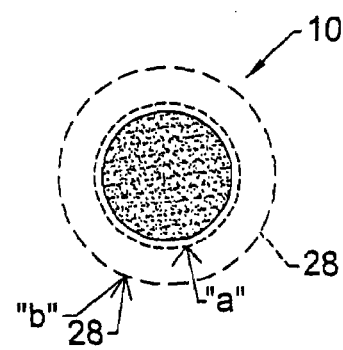
FIG. 9D is a top view of the device shown in FIG. 9A illustrating temporary securing means used to hold the device in a desired location in the subject during an initial healing period or positioning procedure according to embodiments of the present invention.

As shown in FIG. 9D, the device 10 may be secured to the localized tissue with one or more sutures 28. This may include the use of a continuous first boundary suture at position "a" can extend about the root of the mesh collar (the position adjacent the wall of the primary body) so that the side of the mesh collar facing the skin edge can be sutured to the root of the mesh collar (such as with 4-0 polypropylene thread). The ends of the tight boundary suture (the suture adjacent the primary body) can be left without a knot to avoid spacing the device and the skin. Another (outer) suture may be positioned spaced apart from the first boundary suture (shown at position "b" in FIG. 9D). This outer suture may be about 1 cm from the perimeter of the primary body to facilitate the skin edge contacting the device edge during the healing process. A continuous suture of 3-0 polypropylene can be used. The outer suture may protect the free end of the boundary suture. The operative site can be dressed with gauze to absorb fluid and to protect the wound. Skin sutures can be removed after 5–14 days or so after implantation.

Turning now to FIGS. 10A–10D, in certain embodiments, the device 10 can include a skin stop collar 20, which can be employed, with the mesh collar 12. In some skin stop collar 20 embodiments, tissue connectors 30 may be used (such as above and/or below the mesh collar 12) but are not required. In the embodiment shown in FIG. 10B, the tissue connectors are arranged above the mesh collar 12 so as to engage with skin 200. The skin stop collar 20 can be arranged adjacent but below the mesh collar 12. In certain embodiments, the skin stop collar 20 has an increased rigidity over that of the overlying mesh collar 12. In some embodiments, the mesh collar 12 is resilient or flexible and relatively "soft" and/or conformable while the skin stop collar 20 is substantially rigid. The skin stop collar 20 can be narrow and sized with a skirt width, which is less than the skirt width of the mesh collar. In some embodiments, the skin stop collar 20 is on the order of between about 30%–60% less than the width of the mesh collar 12. The skin stop collar 20 can be formed of a biocompatible metal mesh such as a stainless steel mesh having a mesh density of about 50–100 apertures/cm$^2$.

Figure 10A:
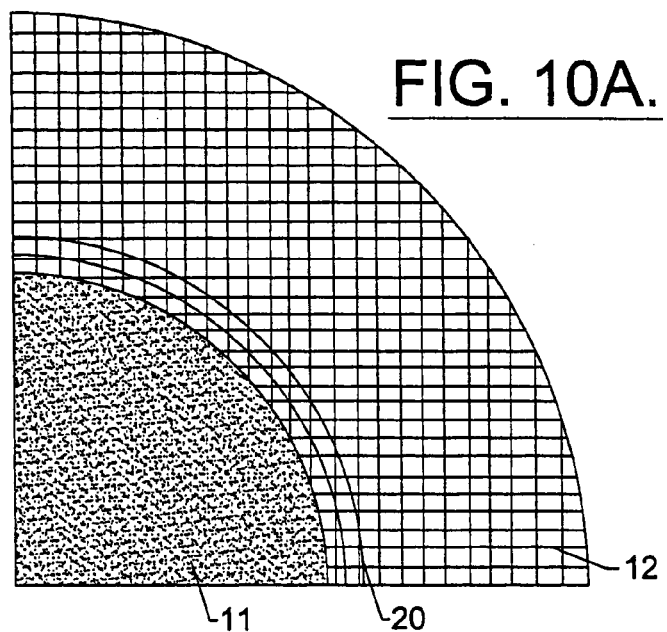
FIG. 10A is a partial top view of a device of another embodiment of the present invention, which is similar to that shown in FIGS. 9A–9D.
Figure 10B:
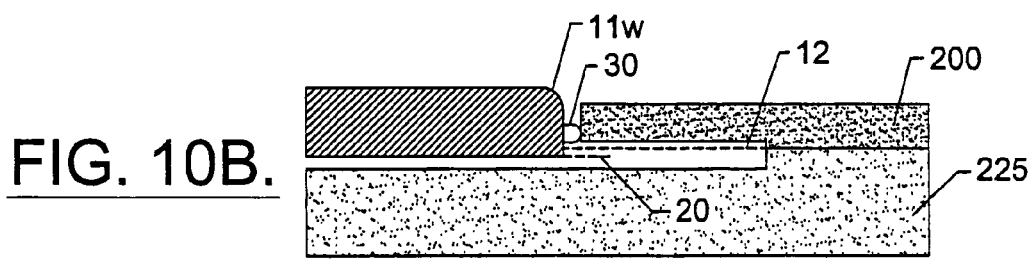
FIG. 10B is a partial side view of the device shown in FIG. 10A during the initial placement period in the subject.
Figure 10C:
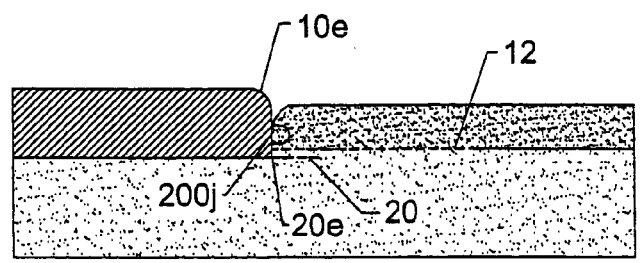
FIG. 10C is a partial side view of the device shown in FIG. 10A in position in the subject after a healing period according to embodiments the present invention.
Figure 10D:
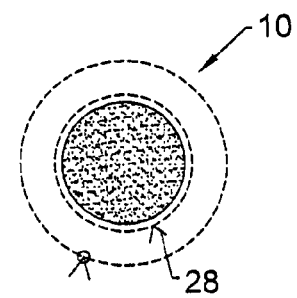
FIG. 10D is a top view of the device shown in FIG. 10A illustrating temporary securing means used to hold the device in a desired location in the subject during an initial healing period or positioning procedure according to embodiments of the present invention.
Figure 11:
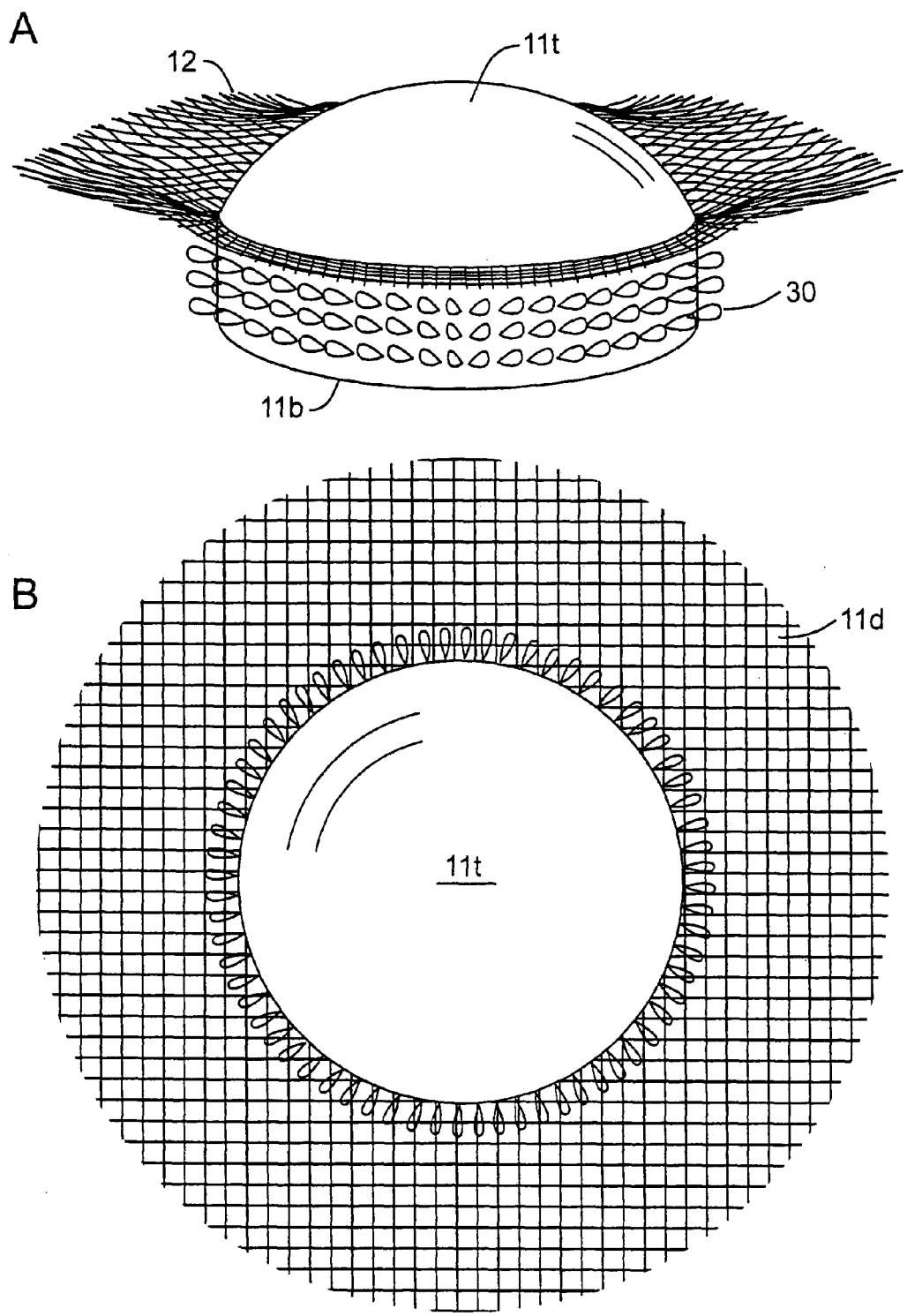
FIG. 11A is an enlarged side perspective view of one percutaneous barrier or access device according to an embodiment of the present invention (similar to those shown in FIGS. 9 and 10).
FIG. 11B is a partial top view of the device illustrated in FIG. 11A.

FIGS. 10A–C illustrate that the skin stop collar 20 is attached to the primary body wall 11w just beneath the mesh collar 12. The inner edge 20e of the skin stop collar can be attached to the primary body 11 such that it presents a smooth profile to inhibit tissue damage from contact with sharp edges of the metal mesh. The smooth profile can be provided by positioning a substrate material over or coating the rough surfaces of the skin stop collar 20 and/or the joint region between the skin stop collar 20 and the primary body wall 11w. FIG. 10B illustrates the initial placement and/or healing period and FIG. 10C illustrates the biosealed condition of the device 100 in the subject after the initial healing period. As shown, the mesh collar 12 is arranged to contact the skin 200 while the skin stop collar 20 is positioned thereunder to help inhibit the downward movement of the sealing junction 200j proximate the wall of the primary body and/or to help support the mesh collar 12.

In some embodiments, the device edge 10e (the top portion proximate the skin in the sealing junction region 200j) can be positioned in the subject so that the edge portion is substantially level with the surface of the skin (FIG. 10C). In certain embodiments, the primary body 11 may be devoid of a subcutaneously positioned tissue connector(s) 30 allowing implantation at sites deficient in adipose tissue. The amount of adipose tissue proximate the device can, in some embodiments, affect the bioconnection of the device and skin (based on migration or movement of the device in the subject over time). Bioconnection shift can occur in an upward or downward direction. The downshift can result when the tissue bed is not deep enough and upward shift can occur when the device body is implanted into deep tissue such that the surface of the edge of the device 10e is lower than the normal skin level.

Turning back to the tissue connectors 30 (e.g., FIGS. 1–4 etc.), in some embodiments, the tissue connectors 30 can be a relatively dense mat of loops, rings, hooks (whether circular or otherwise shaped), or other connective or tissue locking configurations which are disposed about the perimeter wall or walls of the primary body 11 about one or more planes. The dense mat may include at between about 10–500 tissue connectors 30 per square centimeter. In one embodiment, the tissue connectors 30 can be hooks formed from DACRON fabric (similar to the mating portion of a VELCRO attachment structure) having a hook or loop orifice diameter of about 1 mm and arranged on the fabric at about 49 hooks per square centimeter. Other materials, preferably those having flexibility but with sufficient structural rigidity or stiffness to help anchor the device 10, can also be used, such as, but not limited to, other fabrics or elastomeric or polymer materials such as PVC, nylon, rubber, as well as metals (the metals may be coated or treated with a polymer or other material to inhibit sharp contact damage with the localized tissue) and the like. As noted above, the tissue connectors 30 can be formed from or coated with a biocompatible material suitable for long-term indwelling applications.

The tissue connectors 30 can be arranged to extend about a portion of the device 10, such as intermediate the mesh collar 12 and the bottom 11b of the device as shown in FIGS. 7C and 9C. The tissue connectors 30 can be arranged on the primary body 11 to extend substantially about the entire lower portion of the device 10 as shown in FIGS. 7C and 18B. The tissue connectors 30 can be arranged to extend in a single direction with the openings aligned as shown for example in FIG. 3A, 4A, 5A or 14e. In other embodiments, the tissue connectors 30 can be oriented such that their apertures 30a (or pores) face different directions (not shown). Further, although shown as configuring the tissue connectors the same within the described embodiments, the device 10 may include a series of differently configured tissue connectors 30 (not shown). For example, the tissue connectors 30 may be arranged at different extension distances and with different connector features such as, but not limited to a mixture of loops and hooks, or as a double eyelet or as overlapping loops or hooks. Other configurations may also be used such as forks, claws, rectangular bodies defining the aperture whether closed or providing an opening or discontinuity along one side thereof, and the like (not shown).

The tissue connectors 30 can be formed as substantially rigid or semi-rigid members. In some embodiments, the tissue connectors 30 are arranged about the lower portion of the outer surface of the device body 11. The connectors 30 can be resilient and yet sufficiently rigid so as to be able to substantially retain their shape in situ so as to provide suitable anchoring and structural support for the device. By configuring the connectors 30 as rigid or semi-rigid members, the rings, hooks, or other connective element can retain its shape and position even when exposed to tissue under stress. For example, the fibers used to form a connector ring or loop configuration may be configured to slow the cutting effect for local tissue to allow the tissue to engage with the device and provide a stronger mechanical connection therebetween. The tissue connectors 30 may also be configured to slow the cutting effect in a manner which may allow some tissue shifting on the outer surface of the perimeter device without damaging or minimally impacting the bioconnection therea (i.e., at a cell degeneration zone).

The tissue connectors 30 can be formed with fiber sizes or materials which are selected to be sufficiently thick so as to avoid tissue fast cutting even when the device is exposed to reasonable damaging (impact) forces. In addition, the connectors 30 may be configured to be sufficiently thin to reduce the area that the connecting structure takes up proximate the perimeter wall of the device (at the junction layer 5j). In certain embodiments, the fiber strength (the unit strength of the fiber/the fiber cross sectional area) can be selected to match or correspond to the localized connected tissue (the unit strength of the tissue by the area of the size of the gap or aperture). The diameter or width of the aperture of the connector 30 is preferably much larger than the diameter of the fiber which is used to form the connector 30. This allows the tissue to reside over a larger space percentage at the junction layer 5j at the perimeter wall of the device.

In certain embodiments, the connectors 30 can cover the lower surface or the bottom edge portion of the device 10, such as the bottom surface of an enclosed primary body as shown in FIG. 18B.

Figure 12A:
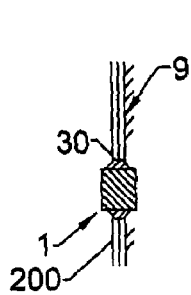
FIGS. 12A–12H are schematic illustrations of exemplary applications for devices provided by the present invention. The devices shown are for purposes of illustration only and the shape, size, and features of the devices shown therein are not to be construed as limiting the configurations of the invention that are described herein.
Figure 12B:
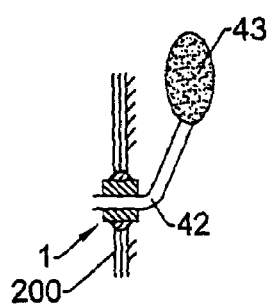

FIGS. 12A–H illustrate some exemplary applications for various embodiments of implantable objects and percutaneous devices according to the present invention. For each, the tissue locking structures 1 can include one or more of tissue connectors 30 and/or mesh collars 12 in various configurations. FIG. 12A illustrates a basic medical object implanted in a subject. The object may include a transparent plate to observe development of living tissue underneath or for plastic reconstruction purposes. FIG. 12B illustrates the device provides connection to tubing or catheter 42 to an artificial or natural organ 43. The tubing 42 can provide the connection for peritoneal dialysis and/or the catheter can provide long-term blood sampling or medicinal infusion.

Figure 12C:
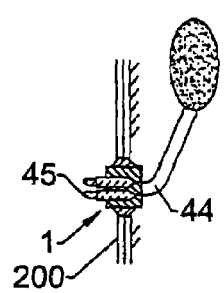
Figure 12D:
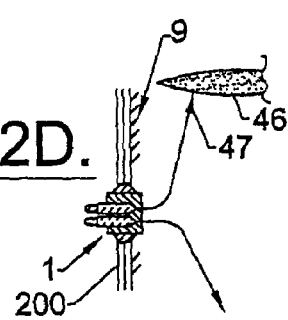

FIG. 12C illustrates the implanted object can provide wire(s) 44 for engagement to an external power supply through a plug(s) 45 to an artificial heart or implanted defibrillation or pacing device. FIG. 12D can provide electrical connections for a bio-signal recording electrode 47 to a muscle 46. The recorded signal may serve to control an artificial limb.

Figure 12E:
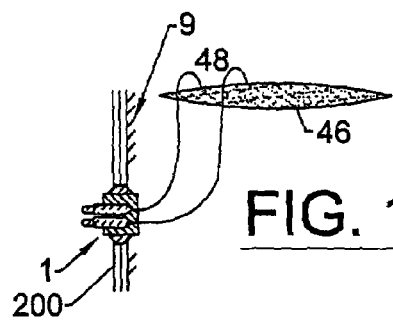
Figure 12F:
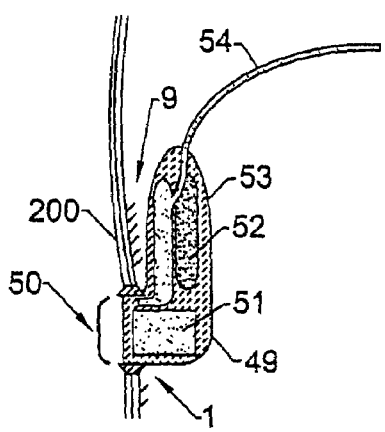

FIG. 12E illustrates a stimulation electrode 48 where an artificial signal may stimulate a desired nerve for a treatment of a disease. FIG. 12F illustrates a bag or case 53 implanted under the skin 200. A lid or closing member 50 can cover the bag about the skin 200. The bag 53 may hold medical equipment 52, battery 51, and/or medicine 53. The device may provide long term automatic infusion to an infusing catheter 54 (such as to delivery medicines like insulin or other fluids) or to provide signal collection or a radio system for distance monitoring.

Figure 12G:
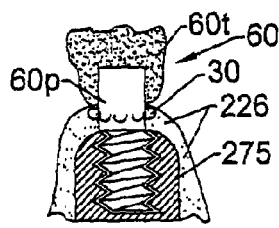

FIG. 12G illustrates a dental implant 60 which may provide support for an artificial crown or tooth 60t. The implant 60 may include tissue connectors 30 configured to engage with localized soft tissue below the bone 275. The soft tissue connectors 30 can connect the gum tissue 226 with the metal post 60p and the artificial tooth 60t.

Figure 12H:
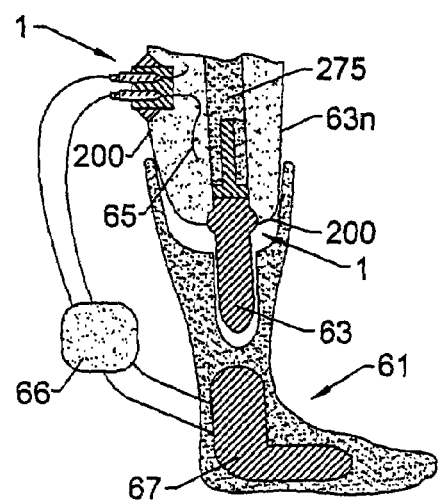

FIG. 12H illustrates an artificial limb 63 with a skeletal extension bar 63 extending through the skin 200. The artificial limb is attached to the truncated portion of a limb 63n. A support member extends into the bone 275 of the truncated limb 63n and extends down or out to engage with the artificial limb 63. A myoelectric signal or recording wire 65 can extend to an externally located power supply and computer control system 66 to control the movement of the artificial joint 67. As such, locked tissue connecting structures 1 (including tissue connectors 30 or mesh collars 12) of the present invention can be used at two locations for the two implant devices (the power and the support structures).

Figure 13A:
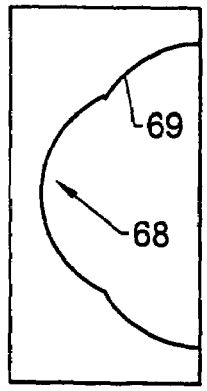
FIGS. 13A–E are enlarged side views of the front portion of an eye (shown as a human eye) illustrating the implantation of an artificial cornea with a tissue connecting structure according to certain embodiments of the present invention.
Figure 13B:
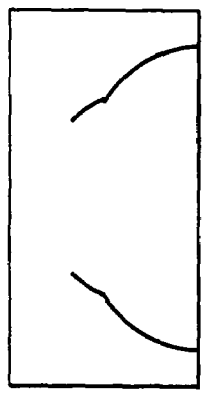
Figure 13C:
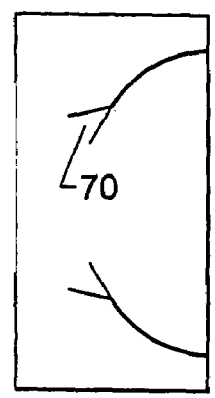
Figure 13D:
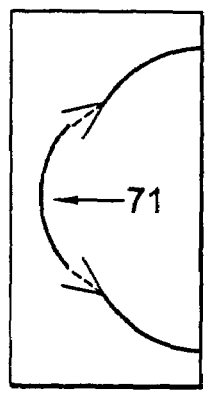
Figure 13E:
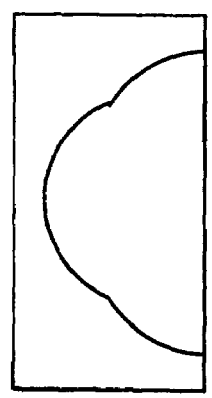

FIGS. 13A–E illustrate the use of a locked connecting structure with an artificial cornea. As shown, the eye includes a cornea 68 and a sclera and conjunctiva 69. To position the artificial cornea in a subject, the cornea is partially of fully resected (FIG. 13B). Next, the cornea 68 can be split into two layers or the conjunctiva can be freed from the sclera 70. The artificial cornea 71 can be placed with the desired tissue connecting structure 30 or 12 so that the structure lies between the two spaces. Sutures or other connecting means can hold the eye tissue thereto. In a preferred embodiment, the artificial cornea employs a mesh collar 12. FIG. 13E illustrates the eye with the artificial cornea as it may appear after healing.

FIGS. 14A–H illustrate an elongated pin 400 which may include a screw portion 410 (to engage with bone 275) includes a plurality of circumferentially arranged outwardly extending tissue connectors 430 thereon. The connectors 430 can be configured with discontinuous perimeter 430d similar to the hook embodiment discussed for FIG. 4A. The discontinuous perimeter can be provided by partially open hooks which can take on the shape of a "7", cane, or "wave" as shown in FIGS. 14A, 14E, and 14F, respectively. Other configurations may also be used.

The tissue connectors 430 are preferably configured to be able to engage with localized biomaterial when in position in the subject. The tissue connectors 430 can be circumferentially arranged on the outer surface of the pin so that the hooks 430d are arranged in a relatively dense configuration of at least about 10–200 hooks per row or 10–200 hooks per square cm about a desired portion or length of the pin. In some embodiments, about 50–100 hooks per row can be used. FIG. 14A illustrates that a plurality series of rings of tissue connectors 430 can be arranged about adjacent or spaced apart portions of the pin body 400 and located on the pin such that they can engage with skin and/or subcutaneous tissue 200, 225 as desired. Preferably, an additional number of tissue connectors 430 extend outside the body proximate the skin layer as discussed for the embodiment shown in FIG. 8. The connectors 430 can be configured and sized with aperture sizes similar to the tissue connectors 30 described above.

In operation, the pin and tissue connectors 430 reside in the patient typically in or proximate soft tissue, or even in bone structure 275, which may help stabilize the pin. To remove, the pin 400 can be moved or rotated as shown by the arrow in FIGS. 14G and H to dislodge the localized tissue 9 or biomaterial from the connectors 430 without requiring incision and may also inhibit damage to the localized biomaterial or tissue. In operation, the biomaterial can be disengaged and released from the opening in or the discontinuous region 430d of the tissue connector 430 responsive to rotation of the pin 400 in a predetermined direction. That is, by orienting the hooks 430 such that the continuous perimeter portion of the hook 430c is the forwardmost portion corresponding to the movement direction when the device is moved or turned will allow the tissue to slip from the connectors 430.

Figure 15A:
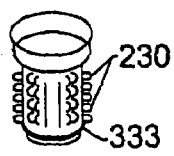
FIG. 15A is a perspective view of a device with a locked connecting structure for objects which connect to bone and extend through the surface of the skin which provides depth adjustability in the subject, according to embodiments of the present invention. The device can be used with skeletal extension bars to connect artificial limbs.
Figure 15B:
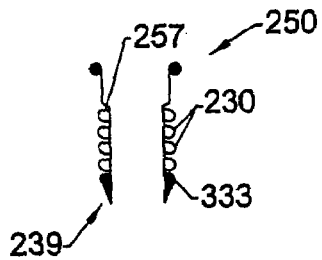
FIG. 15B is a section view of the device of FIG. 15A.
Figure 15C:
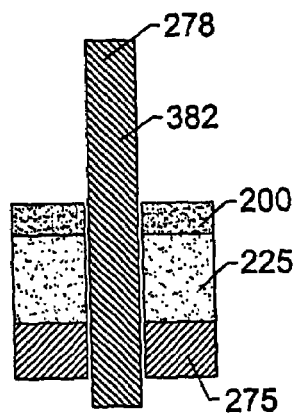
FIGS. 15C–15H schematically illustrate the device of FIG. 15A as used with an implantable elongated stabilizing pin or bar positioned in bone and extending through soft tissue and out of the skin of the subject according to embodiments of the present invention.
Figure 15D:
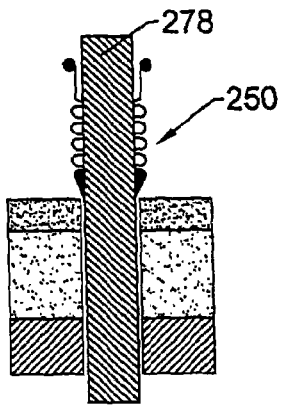
Figure 15E:
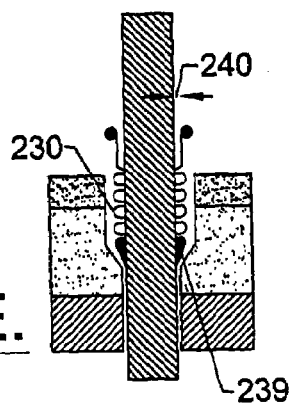

FIGS. 15A–H illustrate a locked connecting device 250 with depth adjustability. This device can be used with medical support bars or pins which are fixed to bone 275. As shown, the device 250 can be used with a skeletal extension bar 278. FIGS. 15A and 15B illustrate that the device 250 has a primary body 257 with a plurality of tissue connectors 230 positioned on an external surface thereof. The device 250 also includes a sealing means 333 such as an O-ring adjacent the proximal most portion of the device (the portion which will reside in the body). The forwardmost or proximal edge portion includes a tissue pusher 239, which can be tapered to increase axially in size, from the forward to the rearward direction, to allow tissue to be directed away from the body of the device as it is inserted into the body. The outermost (or distal) portion can flare outwardly from the tissue connectors 230 to define a cavity or sealable space 240 extending between the body of the skeletal member 278 as shown in FIG. 15E. In certain embodiments, the device 250 can be sealed against the body of the pin 278 to inhibit fluid from migrating between the pin body and the inside of the device.

Figure 15F:
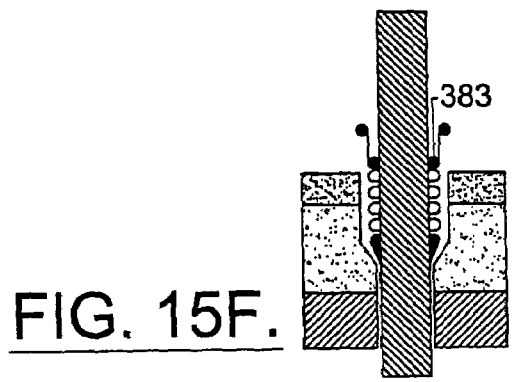
Figure 15G:
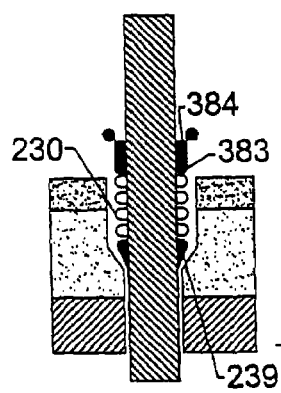
Figure 15H:
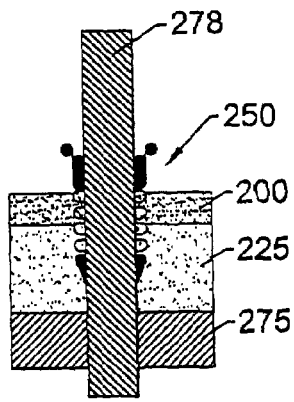

In certain embodiments, an outer sealant such as an O-ring 383 can be positioned into the sealing space 240 as shown in FIG. 15F and then a sealant 384 such as an adhesive or glue can be used to fill any cavity remaining between the connection member body to thus close the remainder (outermost portion) of the cavity space to assure a sealed space. The pin or bar 278 may be used to treat bone conditions to provide stability for fractures, fragments, or support for frail bones, and the like, according to other embodiments of the present invention. If the length of the pin extending from the subject needs adjusting, it can be pulled or pushed through the device 250 without significantly disrupting the localized subcutaneous or skin tissue 225, 200.

The pin 278 can be inserted into bone 275 and the device 250 inserted on the outside thereof in a snugly abutting manner. The pin 250 may be trimmed to fit adjacent the subject's body. Alternatively, the device 250 may be integrally formed onto or sealed against the pin body 278 itself. As shown, the subcutaneous tissue 225 and the skin 200 engage with the tissue connectors 230 extending outwardly from the connection member primary body 257 to help anchor the pin in the subject and to provide a bioconnection and sealing junction which can inhibit discomfort and skin irritation forming in the subject. The tissue connectors 230 can be configured as described for the other tissue connector 30 embodiments above.

In operation, in the embodiment shown, the locked connecting device 250 can be placed onto the outer body of the pin or bar 278. The device 250 with the bar attached can be pushed through the skin 200 and the subcutaneous tissue 225. When in position, the O-ring or gasket or other sealing means 383 can be inserted into the device cavity 240 and the adhesive or glue inserted thereafter.

FIGS. 16A–16E illustrate embodiments of another skeletal extension device 150. The skeletal extension device 150 includes a tissue connection member 175, a proximal threaded member 178 and a distal threaded member 180. The proximal threaded member 178 is sized and configured to be directly threadably attached to the bone 275 of the subject. That is, the proximal threaded member 178 can be rotatably driven into the skeletal structure to which a prosthetic or artificial limb (not shown) is to be attached. In position, the proximal threaded 178 member resides inside the subject. The distal threaded member 180 can include more finely configured threads and is configured, in position, to extend outside the body of the subject. The desired prosthesis can be threaded to the distal threaded member 180. The proximal and distal threaded members 178, 180 can be attached to both rotate concurrently to advance the proximal threaded member into the bone via rotation of the distal member 180. Alternatively, the proximal threaded member and distal can be independently operated such that each is independently advanceable and retractable about the center body 175. For example, the proximal member 178 can be inserted into the subject disposed in the tissue connector member 175 and after the proximal member is advanced into position in the bone, the distal member 180 can be attached to the top or exposed portion of the tissue connector member 175.

As shown in FIG. 16B, the tissue connection member 175 can include an upper portion with a lip 176 which rises above the surface of the skin 200 and subcutaneous tissue connectors 330 attached to the outer wall 175w to which the growing tissue attaches over time as shown from the structural bioconnection 276 provided by the tissue engaging with the tissue connection member (see FIGS. 1–5).

As shown in FIG. 16F, the tissue junction may form directly against the tissue connection member 175 and the device need not include an external 11p portion. In any event, the tissue/device bio-sealing junction 200j forms about the device about the tissue connectors 330 and at the surface of the skin 200.

The tissue connection member 175 includes a plurality of tissue connectors 330 arranged about the outer perimeter wall 175w thereof. The tissue connectors 330 can be formed from fabric, elastomeric, or metal (coated or uncoated) and may be configured in a number of structural tissue interlockable configurations such as, but not limited to, hooks, rings, loops, or eyelets as discussed for the tissue connectors 30 above. In certain embodiments, the connectors 330 can be made similar to those described for the tissue connectors 30 above. For example, the connectors 230 may be made from polymer fiber rings or loops (such as NYLON or DACRON) which extend about substantially the entire length (or width) of the wall 175w of the tissue connection member 175. In some embodiments, the connectors 330 can extend a distance above the normal level of the skin.

In certain embodiments, the tissue connectors 330 can be arranged in a density of between about 10–200 elements per $cm^2$, and preferably about 30–80 elements per $cm^2$. The ring or hook or otherwise configured connector aperture can have an area on the order of about 0.05–5 mm2, and preferably on the order of about 1–2 mm². In other embodiments the aperture width can be on the order of about 0.2–4 mm, and typically about 1–2 mm.

The body of the tissue connection member 175 can be formed from a number of suitable materials selected so as to be biocompatible and to be able to sustain the loading of the skeletal structure and prosthetic limb. Examples of some materials include elastomers, metals, resin reinforced composite materials and the like. Biocompatible coatings may be used as desired. As above, the device can be configured for long term indwelling service.

As shown, the device 150 transfers the weight or body load through the skeletal bone to the aligned threaded members 178, 180 via the tissue connector 175 and directly to the attached prosthesis. Thus, unlike conventional devices, soft tissue is not positioned in the load or access path, which may reduce the discomfort and skin infection rate associated with the use of the device over time.

The device 150 may also employ a substructure member (not shown) which can be inserted and secured in the intramedullary canal of the bone and into which the proximal threaded member 178 may attach. This may be beneficial for subjects having low bone mass or osteoporotic conditions. In addition, the two threaded members 178, 180 may be configured as other types of attachable mechanical structures (such as an extension bar, which can be smooth and tapered and configured to frictionally engage with the bone). In certain embodiments, the tissue connection member 175 may also include one or more of the mesh collar 12 and/or skin stop collar 20 as described above.

In certain embodiments/applications, to position the device 150 in the subject, a portion of the bone into which the device 150 will be inserted may be amputated and the bone prepared and/or bored as needed (FIG. 16A). The proximal threaded member 178 can then be driven into position in the bone and fixed thereto. In certain embodiments, laterally extending attachment pins may be inserted through the proximal threaded or extension member as desired for additional support. In any event, the skin can be sutured or otherwise closed proximate the device and the wound covered for healing. The prostheses can be connected to the distal extension member 180. In the embodiment shown, the prosthesis can be configured with female threads and configured and sized to threadably receive the distal member 180 (typically after the wound has healed and/or after the subcutaneous tissue advances to engage with the tissue connectors 330).

Figure 17A:
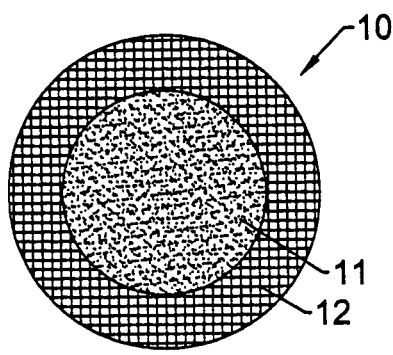
FIG. 17A is a top view of a device according to embodiments of the present invention.
Figure 17B:
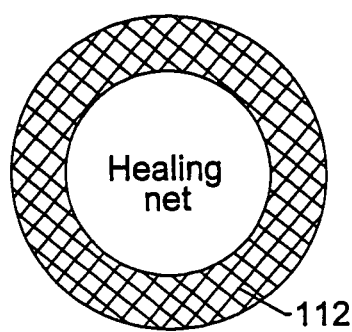
FIG. 17B is a top view of a healing net which can be used to provide external skin support for the implanted device according to embodiments of the present invention.
Figure 17C:
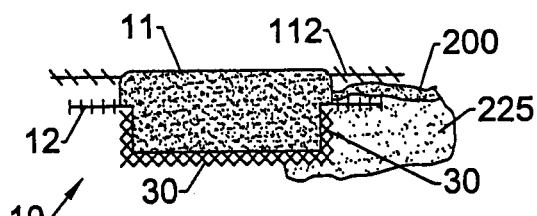
FIG. 17C is a side view of the device shown in FIG. 17A in position in the subject beneath the device shown in FIG. 17B.

As shown in FIGS. 17B–17C, after the device 10 is positioned in the desired location in the subject, a healing net 112, which can have an opening formed therein to allow the top portion of the device 10 to extend therethrough, can be positioned on the outer surface of the skin in alignment with the mesh collar 12 which is residing under the skin. The healing net 112 can be structurally connected (such as via sutures) to the underlying mesh screen and the intermediate tissue to help promote tissue growth in this region. Alternatively, the healing net 112 may be adhesively attached to the outside skin of the subject and weights attached thereto (or the healing net 112 may be configured with sufficient weight) to provide a compressive force against the underlying mesh collar and intermediate tissue/skin. The healing net 112 can be removed typically within 5–10 days after implantation. The healing net 112 may be formed of any suitable material including one or more of an elastomeric or metal material.

Figure 18A:
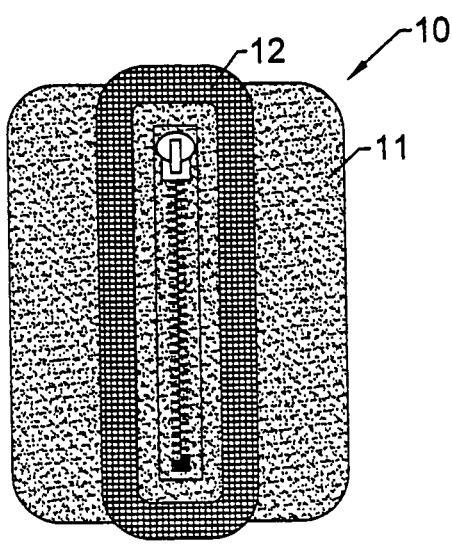
FIG. 18A is a top view of a percutaneous access device, which may be configured as a resilient implantable medicinal delivery bag according to embodiments of the present invention.
Figure 18B:
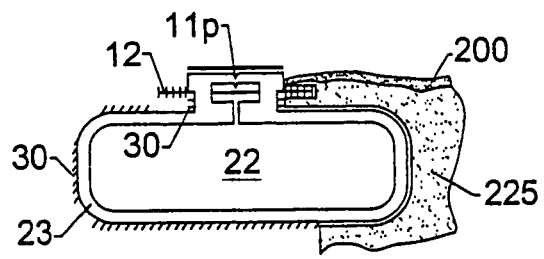
FIG. 18B is a side section view of the device of FIG. 18A.

FIGS. 18A and 18B illustrate that the primary body 11' can be substantially rectangular (preferably with rounded edges) and define an enclosed function space 22. The mesh collar 12 can be arranged as a rounded oval about a top portion of the primary body 11 so as to extend outwardly from the primary body 11t about the access port 11p. The functional space 22 may be defined by a rigid external body, or in some embodiments, as shown, may be a bag 23. The bag 23 may be sealed by an interlocking top seam (shown as a zipper 24) or other securing means as is known to those of skill in the art. Tape, a lid, or other structural protection can be added to help inhibit inadvertent opening or puncture of the bag or seam.

In certain embodiments, the primary body 11 defines a sealable access port 11p. As such, the primary body 11 may include a detachable top portion to provide internal access through the through the access port (without the need for surgery or incisions which disrupt the skin barrier). The detachable top portion 11t can be configured in a number of ways to enclose and seal the access port 11p from the environment. For example, a resilient bag or cover, such as shown in FIGS. 7 and 12F, can securely attach to the top portion of the primary body 11. In other embodiments, a stationary plug, such as a rigid, solid, substantially impermeable (such as glass or marble) member as shown in FIG. 12A can be configured to extend all the way (or a substantial portion of the way) through the access port 11p of the primary body 11. In other embodiments, the device primary body 11 may be sealed about wires, leads, conduits or other components extending therethrough and out the top portion 11t of the device primary body 11.

In certain embodiments, the primary body 11 may include an upper 11p portion 16. The lip portion 16 can define a gradual contoured surface extending between the outer edge of the primary body adjacent the skin layer 200 and the mesh collar 12 to allow the skin to grow over the mesh collar 12 and form the sealing junction 200j with the lip portion 16 as shown in FIG. 6C. In certain embodiments, the lip portion 16 can be configured with an undercut or gap, or to extend a further distance than the underlying wall 11w so as to receive the inner edge of the mesh collar 12 therein (not shown).

In some embodiments, the device can be sized sufficiently small in width or diameter with respect to the implantation site or subject size to inhibit downshift or upshift. In other embodiments, the device edge portion 10e or primary body 11 may be formed from a flexible or lightweight material to inhibit the amount of internal force introduced onto the underlying or proximate tissue. The rigidity of the mesh collar 12 may also be increased so as to have increased rigidity but yet still be resiliently configured. In addition, as discussed above, the skin stop collar 20 can be used beneath the mesh collar 12. The latter may be particularly suitable for implant regions deficient in adipose tissue. In addition, for embodiments configured for adipose tissue deficient regions, the edge of the device may be configured without a lip portion 16.

As shown in FIG. 19, the skin of the subject can be resected to free the edge of the skin from the underlying subcutaneous tissue such that the skin has an opening width sufficient to allow placement of the device therethrough (Block 300). In certain embodiments the opening in the skin is sized such that it is smaller than the width of the upper portion of the device 11t. Preferably, the skin resection or incision should be about 60–75% of the width (or diameter) of the top portion of the device. The tissue bed can be formed by separating the fat out to the midline. The device primary body with an outwardly extending mesh collar 12 can then be positioned in the subject through the resected opening such that the mesh collar 12 is located between the freed skin and the subcutaneous tissue in a manner which allows the mesh collar to engage with (contact) the bottom surface of the skin (Block 310). As shown in FIG. 9D, the device 10 may be secured to the localized tissue with one or more sutures 28. As shown in FIG. 9D, a continuous first boundary suture at position "a" can extend about the root of the mesh collar (the position adjacent the wall of the primary body) so that the side of the mesh collar facing the skin edge can be sutured to the root of the mesh collar (such as with 4-0 polypropylene thread). The ends of the tight boundary suture (the suture adjacent the primary body) can be left without a knot to avoid spacing the device and the skin. Another (outer) suture may be positioned spaced apart from the first boundary suture (shown at position "b" in FIG. 9D). This outer suture may be about 1 cm from the perimeter of the primary body to facilitate the skin edge contacting the device edge during the healing process. A continuous suture of 3-0 polypropylene can be used. The outer suture may protect the free end of the boundary suture. The operative site can be dressed with gauze to absorb fluid and to protect the wound. Skin sutures can be removed after 5–14 days or so after implantation.

The device may also alternatively or additionally comprise tissue connectors such as hooks, loops, or rings as described above. Care should be taken to avoid introducing a risk of infection during healing which may be inadvertently caused by squeezing the suture line about the device body as serous fluid may accumulate on the lower body (particularly when subcutaneous rings or hooks are employed).

The device may include a skin stop collar and the method may include the step of implanting the device in a region deficient in adipose tissue (Block 312).

The invention will now be illustrated with reference to certain examples which are included herein for the purposes of illustration only, and which are not intended to be limiting of the invention.

EXAMPLE 1

Structure, Material, and Method

This study was approved by the Animal Care and Use Committee (East Carolina University School of Medicine), and the care and handling of animals were in accord with national Institutes of Health guidelines.

The LPD-I device tested ("locking percutaneous device") had two portions. The solid clear plexiglass dome was a prototype simulating any medically necessary device. The dome diameter studied ranged from 2.3–2.7 cm, the thickness at the edge was approximately 0.7 cm, and at its center 1.1 cm. The second portion of the LPD-I was the connecting structure that included two parts: the skin connector and the subcutaneous connector. FIGS. 11A and 11B are digital images of the studied device.

The skin connector was a mesh collar made from polyester net with 72 eyes/cm$^2$. The diameter of the warp and weft was approximately 0.2 mm. The mesh was structured so that the warp and the weft did not slide over each other, thereby fixing the pore size at 1 mm$^2$. The mesh collar was bound (silk thread) and glued (silicon glue) on the side surface near the top edge around the dome. Collar width was 0.8–1.0 cm.

The subcutaneous connector was made from DACRON fabric, which has rigid DACRON hooks protruding on one side. The hook orifice diameter was approximately 1 mm and each square centimeter contains approximately 49 hooks. The DACRON hook strip part was glued (silicone glue) to the surface around the dome and under the mesh collar.

The implantation area selected for this study was between the left and right scapulas of the rabbit, near the nape because this is a region relatively rich in fat. After anesthesia and surgical skin preparation, the skin (approximately 95% of the dome diameter) was resected and the skin edge freed from the subcutaneous tissue as wide as the mesh collar width. The tissue bed was formed by separating the fat out to the midline. The device was placed into the tissue bed with continuous suture from the corner fat to the root of the mesh collar (closing the dome) with 4-0 absorbable thread and knotted under the net. The mesh collar was then spread under the freed-up skin. The side facing the skin edge was continually sutured to the net root with 4-0 polypropylene thread. The ends of the tight boundary suture were left free to avoid a knot taking up space between the skin and the device. A continuous suture of 3–0 polypropylene was placed approximately 1 cm from the device edge to assure that the skin edge completely contacted the device edge during the healing process and protected the free end of the boundary suture. The operative site was dressed with three layers of gauze to protect the wound and to completely absorb any exuded fluid. The surgical area was dressed and a protective plastic harness was applied to protect the device from being scratched by the animal. No antibiotics were given. Skin sutures were removed at approximately two weeks after implantation. Note: Because serous fluid accumulated in the space between the rings on the subcutaneous connector in the early postoperative phase, it is important to avoid squeezing the suture line and the dome area to help avoid any possible infection.

Results

Four of five implanted rabbits had successful results; the fifth rabbit died four months postimplantation for reasons unrelated to the device. The healing process of the boundary was very similar to the healing of normal surgical wounds. The boundary was strong enough for normal activity at approximately two weeks and the sutures were removed at that time. The boundary became well sealed in approximately one month. At four months postimplantation without antibiotics there was no gross or histologic evidence of boundary damage, tissue infection, or skin downgrowth. Only healthy tissue and rich capillary beds were noted within the mesh collar (FIG. 20). Observation revealed no gross evidence of boundary damage, tissue inflammation, or skin downgrowth around the implanted devices for more then 8 months without antibiotic administration.

Discussion

A successful percutaneous device should have a strong bioboundary between the device and skin. More important is achieving a strong bioboundary that will grow between the skin and the device. The design of the tissue connecting structure (mesh collar and/or hooks) is the key to this success.

Earlier FPDs had smooth surfaces for both the device and its flange relying on bioadhesive factors. See Topaz et al., *Molded double lumen silicone skin button for drivelines to an artificial heart*, ASAIO Trans. 37 (3); M222–M223, 1991; Kantrowitz et al., *Development of a percutaneous access device*, Trans. Am. Soc. Artif. Intern. Organs, 26, 444–449, 1980. This resulted in weak connections, skin downgrowth, and sinus tract formation (see Shin et al., *Tissue reactions to various percutaneous materials with*

*different surface properties and structures*, Artif. Organs, 21(9); 995–1001, 1997; Lundigren et al., *Soft-tissue anchored percutaneous device for long-term intracorporeal access*, J. Invest. Surg., 2(1); 17–27, 1989), a main source of infection. The later FPD had several holes through the flange. See Bailie et al., *Vascular-access-port implantation serial blood sampling in conscious swine*, Lab. Anim. Sci. 36(4); 431–433, 1986. The holes function to secure the tissue and limit its movement, helping to prevent injury to the boundary area.

The conventional APD with its rough device surface increased the area of the bioadhesive boundary and produced friction from movement of the anchored tissue. See Daley et al., *A new percutaneous access device for peritoneal dialysis*, ASAIO Trans., 33(3); 664–671, 1987; Daly, B. D., *Percutaneous access for peritoneal dialysis*, ASAIO Trans., 34(9); 932–934 1988. Kantrowitz et al., *Development of a new long-term access device for continuous ambulatory peritoneal dialysis*, ASAIO Trans., 34(4); 930–931, 1988; Wredling et al., *Experience of long-term intraperitoneal insulin treatment using a new percutaneous access device*, Diabet. Med., 8(6); 597–600, 1991; Lundigren et al., *Soft-tissue anchored percutaneous device for long-term intracorporeal access*, J. Invest. Surg., 2(1); 17–27, 1989; von Recum, A. F., "Soft tissue implant with micron-scale surface texture to optimize anchorage, U.S. Pat. No. 5,219,361, 1993. However, boundary damage, skin downgrowth, and tissue infection still occurred. See Lundigren et al., *Soft-tissue anchored percutaneous device for long-term intracorporeal access*, J. Invest. Surg., 2(1); 17–27, 1989. The LPD's studied had connecting structure with millimeter size pores where tissue "locks" which can overcome the deficiencies of the prior devices.

The skin connector of the LPD is a strong, thin, and flexible mesh collar surrounded by an abundance of millimeter size pores. The subcutaneous tissue connector contains extruded rigid rings or hooks of millimeter size holes. Some advantages are:

1. Groups of cells can grow through the millimeter size mesh collar pores and subcutaneous extruded rigid rings to lock the tissue and device together to form a strong bioconnection. See Shin et al., *Tissue reactions to various percutaneous materials with different surface properties and structures*, Artif. Organs, 21(9); 995–1001, 1997; Lundigren et al., *Soft-tissue anchored percutaneous device for long-term intracorporeal access*, J. Invest. Surg., 2(1); 17–27, 1989.

2. The histologic finding of abundant capillaries (FIG. 20) confirms that these vessels can grow through the millimeter size net pores. This feature ensures that the connecting tissue has a rich blood supply and can maintain viability.

3. Millimeter size pores are small enough to limit injury of the sealing boundary and prevent skin downgrowth and tissue infection. Gross inspection and histologic observations support this.

4. The device may function immediately after implantation. Initially the connection relies on sutures. Once healing is complete the sutures are removed. The connecting boundary is strong enough to permit the animals normal activities.

The results show that an optimally designed connecting structure can be important to making a strong biomechanical bond between the skin and a foreign body. Such design and technique has the potential to positively impact the care and quality of life for humans who require long-term indwelling devices.

EXAMPLE 2

Structure, Material, and Method

Two types of LPD-II devices were tested. Type 1 had two components, a dome and a skin connector (but without the underlying skin stop collar). The Type 2 device had an extra structure, the SSC (see FIG. 10). The dome was constructed from solid clear plexiglass with a thickness of 0.4 cm and a diameter of 2.3–3.5 cm. The skin connector or mesh collar surrounded the dome. It was made from polyester net with 72 eyes/cm$^2$ and about 0.2 mm diameter of the warp and weft. Its width was approximately 1.3 cm. The SSC was positioned just beneath the mesh collar and was made from stainless steel mesh with 64 eyes/cm$^2$. The wire had a diameter of 0.5 mm and width of approximately 0.4 cm.

The mesh collar of the LPD-II without the SSC (type 1) was attached to the bottom edge of the dome by heating. The mesh collar and SSC (LPD-II type 2) were fixed to the lower edge of the dome simultaneously first by heating and then by application of a layer of thick plexiglass chloroform solution. The edge of the SSC was carefully dipped in the thick plexiglass chloroform solution as well. This created a smooth edge to the SSC to prevent soft tissue damage from the metal wire.

The area between the scapulae near the nape was chosen for implantation. Following surgical skin preparation and administration of a general anesthetic, a circle was drawn on the skin with a surgical marking pen. The diameter of the circle was approximately 10% smaller than the diameter of the dome. The circle of skin was resected and the skin edge was freed from the subcutaneous tissue in an arc as wide as the width of the mesh collar. The device was placed in the skin opening; the mesh collar was spread between the freed skin and subcutaneous tissue. The skin edge was continually sutured to the mesh collar root with 4-0 nylon thread. The suture was placed subcutaneously and tightened, but without a tied knot. The free ends of the suture were about 1.5 cm and were left outside the skin. A second continuous suture was placed in the skin about 0.7 cm from the edge of the dome to ensure that the skin edge would be in close contact with the lateral surface of the dome during healing. The operative site was dressed with gauze. The rabbit was placed in a harness to prevent the animal from scratching the device. No antibiotics were given.

Six rabbits (group 1) were implanted with LPD-II type 1 devices. The remaining five rabbits (group 2) were implanted with LPD-II type 2 devices. Suture "b," the outer suture, was removed at 7–8 days and suture "a," the inner suture, on the 10–12th day after implantation.

Results

The results are shown in Table 1.

Group 1: Air leakage was the main complication for this group after which time the animal was euthanized. Two implantations were successful for more than six months.

Group 2: One rabbit died from an incidental injury at about two months. Four implantations were successful for greater then one year after which this group was electively euthanized.

Discussion

The LPD-I corresponds to the percutaneous device described in EXAMPLE 1, which effectively overcomes the problems of skin downgrowth and infection of prior devices therefore offering a strong connection between the skin and the device. If implanted in humans this device can potentially permit patients greater opportunity to participate in normal activities and minimize the risk of infectious complications. The LPD-I is typically suited for implantation sites where there is adequate adipose tissue under the local skin in which the subcutaneous connector resides. The adipose tissue should be thicker than the device dome edge otherwise bioconnection downshift may occur between the skin and the device. Bioconnection downshift can be differentiated from skin downgrowth (Table 2).

Bioconnection shift may actually occur in both directions, either downward or upward. Downshift results when the tissue bed is not deep enough. Up-shift occurs when the device dome is fixed to deep tissue, such as muscle or bone, and the surface of the dome edge is lower than the normal skin level even at sites where there may be different subcutaneous adipose tissue. The LPD-II which allows implantation at a variety of body sites, even those having deficient amounts of adipose tissue in which to place the device.

It is hypothesized that the length of time that the device functioned was closely related to the weight (W) of the rabbit and the diameter of the domes (D) used in group 1 (Table 1). The smaller the ratio of D/W, the flatter the area around the device. The bigger the D/W ratio, the more convex the area is around the device. In the first example, after early healing, the bioconnection maintained permanent function. In the second example, the early healing has proceeded well because of the suture and the pressure exerted by the wound dressing. However the internal tissue force may cause the bioconnection to produce downshift over time. Under these circumstances, air leakage can occur.

The implantation in rabbit 6 of group 1 (Table 1) lasted more than one year. This may be attributable to the larger size of that rabbit; hence, the dome diameter was relatively small yielding a flatter implantation area. That animal's D/W was the smallest among all study animals. The quality of the bioconnection around the dome on rabbit 6 as seen on day 145 was good. The bioconnection function was still good on day 335, but most of the bioconnection has some downshift with the collar net being exposed. This downshift may be attributed to the device being made manually, resulting in an undesired lip being formed from the healing process under the mesh collar. Alternatively, a very good bioconnection was seen on the portion of the dome of another test device. This connection was formed from a very good local dome structure without a 11$p$ imperfection.

Four possible alternatives may overcome bioconnection downshift: 1) making the device dome as small as possible; 2) making the device dome from soft material (which may prevent the formation of internal force on the tissue); 3) making the mesh collar from a more firm material, and 4) adding the SSC just beneath the soft mesh collar to prevent the bioconnection downshift. The following is a discussion of the fourth method.

Bioconnection downshift occurs on the lateral surface of the dome. The SSC is made from a rigid material that can minimize skin edge and soft mesh collar downshift. The results in group 2 demonstrate that the SSC is helpful. The ratio of D/W in group 2 animals is similar to those rabbits 2, 3 and 4 in group 1 (Table 1); however the bioconnection in group 2 was far superior.

Note that the mesh collar around the dome became exposed in the implantation of the LPD-II with the SSC (type 2). This did not affect the function of the bioconnection; the seal between the device and skin remained intact and the skin edge was in close contact with the device. Actually the skin tissue grew between the mesh collar and the SSC in that area. This occurred for two reasons. The first is that the two layers of net (the SSC net and mesh collar net) not only increase the distance between skin and subcutaneous tissue but also the eyes of one mesh tend to become occluded by the netting of the superimposed mesh. The increased distance and blocked mesh eyes decrease delivery of adequate nutrients and oxygen from subcutaneous tissue to the skin. After about 145–151 days the LPD-I type 1 and LPD-II type 2 have different bioconnection appearances. Increasing the eye size of the SSC may help solve this problem. The second reason is that although the skin site diameter was about ninety percent of the diameter of the device dome, the diameter of the skin opening was larger than that of the dome after skin was removed because of the intrinsic elasticity of the skin. Such skin elasticity may promote mesh collar exposure. To create a defect in the skin sufficient to house a given dome, it is estimated that the skin opening should be approximately sixty to seventy percent of the device dome diameter.

In summary, skin connector can function alone without the subcutaneous tissue connector as a locked percutaneous device where necessary. The LPD-II can be implanted at any site, even one devoid of or deficient in adipose tissue beneath the local skin. In addition, the SSC is helpful in increasing the success rate of the locked percutaneous device when the mesh collar is made from soft material.

TABLE I

The results from the two groups of implantation of LPD-II.

| Rabbits Identification | | | Weight (W) | Dome Diameter (D) | | Duration | |
|---|---|---|---|---|---|---|---|
| Group | Order # | File # | (kg) | (cm) | D/W | (day) | Complication |
| 1 | 1 | 10385 | 3.0 | 3.5 | 1.17 | 37 | air leakage |
| without | 2 | 10386 | 3.0 | 2.3 | 0.17 | 111 | air leakage |
| SSC) | 3 | 10387 | 3.1 | 2.3 | 0.74 | 189 | air leakage |
| | 4 | 10388 | 3.0 | 2.2 | 0.73 | 91 | air leakage |
| | 5 | 10389 | 3.1 | 3.5 | 1.13 | 43 | air leakage |
| | 6 | 11558 | 5.5 | 2.4 | 0.44 | 416 | air leakage |
| 2 | 7 | CR09 | 3.7 | 2.3 | 0.62 | 388 | None |
| (with | 8 | 11494 | 3.2 | 2.3 | 0.68 | 367 | None |
| SSC) | 9 | 11495 | 3.4 | 2.3 | 0.70 | 62 | died from accident |
| | 10 | 11601 | 3.4 | 2.3 | 0.72 | 368 | None |
| | 11 | 11618 | 3.3 | 2.3 | 0.68 | 368 | None |

TABLE 2

The difference between skin downgrowth and bioconnection downshift.

| | Skin Downgrowth | Bioconnection Downshift |
|---|---|---|
| Formation cause | External force | Internal tissue force |
| Force direction | Horizontal to the skin surface | Vertical to the skin surface |
| Force features | Fast and frequent | Slow and continuous |
| Bioconnection | Broken | Keep integrated |
| Infection | Yes | No |

The mechanical or tissue locking connector structures provided by the present invention may be suitable for many uses as described above including, but not limited to, implantable barrier or percutaneous access devices, and for use in locating foreign objects in mucus membranes including artificial corneas in humans, as well as for skeletal and dental implants. The locking connecting structures may help alleviate gum infections associated with some of the conventional dental implant devices. The locking connecting structures of the present invention may be used to help secure the tooth implant in the bone and/or through the gum tissue and to provide support for the tooth at the gum surface. The locking connecting structures may also be suitable for use with internal implantable devices such as artificial heart valves and artificial tendons with or without the use of permanent sutures.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A percutaneous access device configured for implantation into a subject to provide subcutaneous access therethrough, comprising:

a primary body having opposing top and bottom portions, each with a respective outer surface, and at least one sidewall extending therebetween, wherein in position in a subject, said primary body bottom portion resides within the subject and said bottom portion outer surface faces into the subject; and an outwardly extending mesh collar attached to said primary body such that said mesh collar is positioned intermediate said top and bottom portions and extends outwardly from said at least one sidewall a first distance, and wherein, in position in the subject said mesh collar is configured to engage with the skin of a subject, wherein said top portion of said primary body includes a plurality of tissue connectors which extend outwardly from the wall of the primary body, wherein in position, at least some of said tissue connectors reside above the natural level of the skin, and wherein said mesh collar is attached to said primary body beneath said plurality of tissue connectors.

2. A percutaneous access device configured for implantation into a subject to provide subcutaneous access therethrough, comprising:

a primary body having opposing top and bottom portions, each with a respective outer surface, and at least one sidewall extending therebetween, wherein in position in a subject, said primary body bottom portion resides within the subject and said bottom portion outer surface faces into the subject;

an outwardly extending mesh collar attached to said primary body such that said mesh collar is positioned intermediate said top and bottom portions and extends outwardly from said at least one sidewall a first distance, and wherein, in position in the subject, said mesh collar is configured to engage with the skin of a subject; and a plurality of tissue connectors positioned about the perimeter of said primary body below said mesh collar, wherein said tissue connectors extend outwardly from the primary body a distance that is less than that of the collar, and wherein the tissue connectors are sufficiently rigid to be able to substantially maintain their shape and outwardly extending configuration external of a subject.

3. A percutaneous access device according to claim 2, wherein said plurality of tissue connectors are configured to extend outwardly as a plurality of generally outwardly extending discrete rings and/or hooks having an aperture or orifice width of between about 02–4 mm.

4. A percutaneous access device according to claim 3, wherein, in position, said tissue connectors are configured to engage subcutaneous tissue.

5. A percutaneous access device according to claim 4, wherein said tissue connectors are sufficiently rigid so as to substantially retain their shape and outwardly extending configuration in situ when implanted in the subject.

6. A percutaneous access device according to claim 2, wherein said tissue connectors are configured as one or more of hooks and rings.

7. A percutaneous device configured for implantation into a subject to provide subcutaneous access therethrough, comprising:

a primary body having opposing top and bottom portions, each with a respective outer surface, and at least one sidewall extending therebetween and a perimeter associated therewith, wherein in position in a subject, said primary body bottom portion resides within the subject and said bottom portion outer surface faces into the subject;

a mesh collar attached to and extending outwardly from said primary body at a position that is closer to said top portion than said bottom portion, said mesh collar having structural rigidity sufficient to retain a predetermined shape; and a plurality of tissue connectors attached to said primary body and extending outwardly therefrom about a portion of the perimeter thereof, said tissue connectors extending outwardly a smaller distance from the primary body than the mesh collar, wherein, in position, a plurality of the tissue connectors reside below the mesh collar and are adapted to engage with subcutaneous tissue to provide structural attachment for the device, and a plurality of the tissue connectors reside above the mesh collar and are adapted to engage with the skin of the subject to define a bioconnection about a sealing junction defined by the region where the skin meets the perimeter of the primary body.

8. A device according to claim 7, wherein said tissue connectors comprise rings and/or hooks with apertures, said apertures having a width of between about 0.2–4 mm.

9. A device according to claim 8, wherein said tissue connectors are substantially rigid.

10. A device according to claim 8, wherein said tissue connectors are sufficiently rigid such that they are able to substantially retain their shape and position in situ, and wherein the mesh collar is a substantially continuous unitary generally planar sheet.

11. A percutaneous access device according to claim 8, wherein, in position, a portion of said tissue connectors are configured to engage with at least one of subcutaneous tissue, bone, and an internal organ.

12. A percutaneous device configured for implantation into a subject to provide subcutaneous access therethrough, comprising:
a primary body having opposing top and bottom portions, each with a respective outer surface, and at least one sidewall extending therebetween and a perimeter associated therewith, wherein in position in a subject, said primary body bottom portion resides within the subject and said bottom portion outer surface faces into the subject; and
a plurality of tissue connectors attached to said primary body and extending outwardly therefrom about a portion of the perimeter thereof, such that, in position, a plurality of tissue connectors are adapted to engage subcutaneous tissue to provide structural attachment for the device, and a plurality of tissue connectors are adapted to engage the skin of the subject to define a bioconnection about a sealing junction defined by the region where the skin meets the perimeter of the primary body, wherein said tissue connectors are rings with apertures, said apertures having a diameter of about 0.2–4 mm;
wherein, in position, a plurality of said tissue connectors reside above the external surface of the skin.

13. A method of providing a structurally supported bioconnection for a device, comprising the steps of:
implanting a device having a perimeter with a plurality of outwardly extending tissue connectors mounted thereon through an opening in biological subject, each tissue connector defining an aperture sized in width at about 0.2–4 mm, wherein the tissue connectors have sufficient rigidity to be able to retain their shape and outwardly extending configuration in position in situ to thereby lock with local tissue, and wherein the tissue connectors are arranged on the device in a density of between about 10–200 per cm$^2$; and
growing proximately located tissue into proximately located tissue connectors such that the tissue connectors engage with the tissue to define a bioconnection which engages the device with localized tissue in a desired location in the subject.

14. A method according to claim 13, further comprising the step of sealing the device to define a skin bioconnection defined by the attachment of the skin to at least a plurality of the tissue connectors about the perimeter of the upper portion of the implanted device.

15. A method according to claim 14, wherein the device includes a semi-rigid mesh collar located above at least some of the tissue connectors, wherein, said method further comprises the step of positioning the mesh collar adjacent the lower internal surface of the skin such that the skin attaches to the perimeter of the device over the mesh collar and tissue grows trough said mesh collar to close the opening of said implanting step to provide a skin biosealed junction, and wherein the device provides access trough the skin to a subject.

16. A method according to claim 13, wherein said device includes both tissue connectors and a semi-rigid mesh collar, and said growing step includes growing subcutaneous tissue into the tissue connectors and tissue associated with the skin into the mesh collar.

17. A method of locking a foreign object into a biological subject, the foreign object comprising a plurality of outwardly extending tissue connectors connected to the outer perimeter thereof into a biological subject, each of the tissue connectors having an aperture formed therein, the method comprising the step of:
implanting the object into a biological subject such that localized tissue grows into the apertures in the tissue connectors to provide structural support for the object in the biological subject, wherein the tissue connectors are sufficiently rigid so as to be able to substantially retain their shape and outwardly extending configuration in situ, wherein the apertures of the tissue connectors have an opening gap of between about 0.2 mm–5 mm, and wherein the object is adapted to reside in the biological subject for at least 6–12 months.

18. A method according to claim 17, wherein the object comprises a percutaneous access device.

19. A method according to claim 17, where the tissue connectors comprise polymer fibers configured as discrete loops.

20. A method of locking a foreign object into a biological subject, the foreign object comprising a plurality of outwardly extending tissue connectors connected to the outer perimeter thereof into a biological subject, each of the tissue connectors having an aperture formed therein, the method comprising the step of:
implanting the object into a biological subject such that localized tissue grows into the apertures in the tissue connectors to provide structural support for the object in the biological subject, wherein the apertures have an opening gap of between about 0.2 mm–5 mm, wherein the object is adapted to reside in the biological subject for at least 6–12 months, and wherein the tissue connectors are arranged on a portion of the perimeter of the object in a quantity of between about 50–100 per cm$^2$.

21. A method according to claim 20, wherein the tissue connectors are sufficiently rigid so as to be able to retain their shape and outwardly extending configuration in situ, and wherein the tissue connectors are arranged to cover at least a major portion of the perimeter surface of the object.

22. A method according to claim 21, wherein the tissue connectors are configured as at least one of hooks, rings, and loops.

23. A method of locking a foreign object into a biological subject, the foreign object comprising a plurality of outwardly extending tissue connectors connected to the outer perimeter thereof into a biological subject, each of the tissue connectors having an aperture formed therein, the method comprising the step of:
implanting the object into a biological subject such that localized tissue grows into the apertures in the tissue connectors to provide structural support for the object in the biological subject, wherein the apertures have an opening gap of between about 0.2 mm–5 mm, wherein the object is adapted to reside in the biological subject for at least 6–12 months, and wherein the object is adapted to deliver insulin subcutaneously.

24. A method of locking a foreign object into a biological subject, the foreign object comprising a plurality of outwardly extending tissue connectors connected to the outer perimeter thereof into a biological subject, each of the tissue connectors having an aperture formed therein, the method comprising the step of:
implanting the object into a biological subject such that localized tissue grows into the apertures in the tissue connectors to provide structural support for the object in the biological subject, wherein the apertures have an opening gap of between about 0.2 mm–5 mm, wherein the object is adapted to reside in the biological subject for at least 6–12 months, and wherein said object provides connections for peritoneal dialysis.

25. A method of locking a foreign object into a biological subject, the foreign object comprising a plurality of outwardly extending tissue connectors connected to the outer perimeter thereof into a biological subject, each of the tissue connectors having an aperture formed therein, the method comprising the step of:
implanting the object into a biological subject such that localized tissue grows into the apertures in the tissue connectors to provide structural support for the object in the biological subject, wherein the apertures have an opening gap of between about 0.2 mm–5 mm, wherein the object is adapted to reside in the biological subject for at least 6–12 months, and wherein the tissue connectors are substantially rigid.

26. A method of locking a foreign object into a biological subject, the foreign object comprising a plurality of outwardly extending tissue connectors connected to the outer perimeter thereof into a biological subject, each of the tissue connectors having an aperture formed therein, the method comprising the step of:
implanting the object into a biological subject such that localized tissue grows into the apertures in the tissue connectors to provide structural support for the object in the biological subject, wherein the apertures have an opening gap sized between about 0.2 mm–5 mm, wherein the object is adapted to reside in the biological subject for at least 6–12 months, and wherein the tissue connectors have sufficient rigidity to substantially retain their shape in situ.

27. A percutaneous access device configured for implantation into a subject to provide subcutaneous access therethrough, the device being characterized by a plurality of tissue lockable connecting structures having sufficient rigidity so as to be able to maintain a predetermined shape and orientation when external of the subject and when positioned in situ, at least some of the locked structures being located proximate to at least one selected external surface of the device to provide a skin level interface, the tissue lockable connecting structures defining respective air gap spaces sized from between about 0.2–4 mm.

28. A percutaneous skin access device according to claim 27, wherein the device comprises a primary body defining an access passage therein, and wherein the locked connecting structures comprise a thin semi-rigid mesh collar having the gap spaces formed therein, the mesh collar being positioned on the devices such that it radially extends outwardly from the primary body of the device as a unitary generally continuous sheet.

29. A percutaneous skin access device according to claim 27, wherein the device comprises a primary body with at least one sidewall defining an access passage therein, and wherein the tissue lockable connecting structures comprise discrete loops, hooks and/or ring elements formed onto the exterior surface of the primary body with a density of between about 30–90 elements per $cm^2$.

30. A percutaneous skin access device according to claim 27, wherein the device comprises a primary body with at least one sidewall defining an access passage therein, and wherein the locked connecting structures comprise discrete loops, hooks and/or ring elements with a density of between about 30–90 elements per $cm^2$ formed onto a substrate sheet which is attached to the external surface of the device.

31. A percutaneous access device configured for implantation into a subject to provide subcutaneous access therethrough, the device being characterized by a plurality of locked connecting structures located proximate at least one selected external surface thereof, the locked connecting structures defining an air gap space sized from between about 0.2–4 mm,
wherein the device comprises a primary body with sidewalls defining an access passage therein, and wherein the locked connecting structures are a plurality of loops defining the gap spaces and extending outwardly from the primary body of the device.

32. A percutaneous access device configured for implantation into a subject to provide subcutaneous access therethrough, the device being characterized by
a plurality of locked connecting structures located proximate to at least one selected external surface thereof, the locked connecting structures defining an air gap space sized from between about 0.2–4 mm,
wherein the device comprises a primary body with sidewalk defining an access passage therein, and wherein the locked connecting structures are a plurality of hooks defining the gap spaces and extending outwardly from the primary body of the device.

* * * * *

UNITED STATES PATENT AND TRADEMARK OFFICE
CERTIFICATE OF CORRECTION

PATENT NO.        : 7,083,648 B2                                          Page 1 of 1
APPLICATION NO. : 10/398887
DATED             : August 1, 2006
INVENTOR(S)       : Yu et al.

It is certified that error appears in the above-identified patent and that said Letters Patent is hereby corrected as shown below:

Column 30,
Line 34 should read -- orifice width of between about 0.2-4 mm. --

Column 34,
Line 48 should read -- walls defining an access passage therein, and wherein --

Signed and Sealed this

Twenty-eighth Day of November, 2006

JON W. DUDAS
*Director of the United States Patent and Trademark Office*